US011698351B1

(12) United States Patent
Barzanji et al.

(10) Patent No.: US 11,698,351 B1
(45) Date of Patent: Jul. 11, 2023

(54) GAMMA RADIOGRAPHY SYSTEM AND METHOD OF USING A GAMMA RADIOGRAPHY SYSTEM

(71) Applicant: King Abdulaziz University, Jeddah (SA)

(72) Inventors: Eslam Barzanji, Jeddah (SA); Abdulsalam Alhawsawi, Jeddah (SA); Mohammed Siddig, Jeddah (SA); Mohammed Ali M Alawi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/877,386

(22) Filed: Jul. 29, 2022

(51) Int. Cl.
*G21G 4/06* (2006.01)
*G01N 23/10* (2018.01)
*G21F 5/015* (2006.01)

(52) U.S. Cl.
CPC ............. *G01N 23/10* (2013.01); *G21F 5/015* (2013.01); *G21G 4/06* (2013.01); *G01N 2223/1013* (2013.01)

(58) Field of Classification Search
CPC ............ G01N 23/10; G01N 2223/1013; G21F 5/015; G21G 4/06
See application file for complete search history.

(56) References Cited

U.S. PATENT DOCUMENTS

| | | | | |
|---|---|---|---|---|
| 3,567,941 A | * | 3/1971 | Russel | A61B 6/06 378/160 |
| 4,516,256 A | * | 5/1985 | Wapperom | G21F 5/02 250/497.1 |
| 9,101,039 B2 | | 8/2015 | Ikarashi et al. | |

FOREIGN PATENT DOCUMENTS

| | | |
|---|---|---|
| CN | 1586668 A | 3/2005 |
| KR | 10-1318840 | 10/2013 |
| WO | 2017/032345 A1 | 3/2017 |

OTHER PUBLICATIONS

SAYUTI ; Non-Destructive Testing (NDT)—Industrial Radiography Normal Working Procedures ; https://www.slideshare.net/shahar_sayuti/nondestructive-testing-ndt-industrial-radiography-normal-working-procedures ; Apr. 1, 2011 ; 4 Pages.
Taha, et al. ; Feasibility of a Novel Gamma Radiography Mammo System ; Journal of Medical Physics and Applied Sciences, vol. 1, No. 1:3 ; Jan. 17, 2016 ; 8 Pages.
Alyassin, et al. ; Feasibility study of gamma-ray medical radiography ; Applied Radiation and Isotopes 72 ; pp. 16-29 ; Nov. 9, 2012 ; 14 Pages.

* cited by examiner

*Primary Examiner* — Jurie Yun
(74) *Attorney, Agent, or Firm* — Oblon, McClelland, Maier & Neustadt, L.L.P.

(57) ABSTRACT

A gamma radiography system includes a gamma source holder, a shaft handle attached to the source holder, a source container that surrounds the source holder, a source container cover attached to the source container to receive and slidingly support the shaft handle, a shielded housing that detachably receives the source container, and an extension connected to the shielded housing, such that an opening of the extension covers a beam aperture of the shielded housing. The shaft handle is configured to move the gamma source holder between a non-deployed position, in which the gamma source holder is surrounded by the source container, to a deployed position, in which the gamma source holder extends from the source container into the shielded housing.

20 Claims, 22 Drawing Sheets

GAMMA RADIOGRAPHY SYSTEM AND METHOD OF USING A GAMMA RADIOGRAPHY SYSTEM

BACKGROUND

Technical Field

The present disclosure is directed to imaging systems and, more particularly, to gamma-ray radiography imaging systems for medical use.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Research in recent years has proposed the use of gamma-ray in medical radiography. It is believed that a gamma-ray based imaging system is economical than an X-ray machine and requires less maintenance. X-ray machines are electronically complicated, bulky and require high-voltage for their operation. A gamma-ray image, on the other hand, does not need electric power to produce X-rays and needs only mechanical and shielding systems that provide protection and ease of use and handling.

Accordingly, it is one object of the present disclosure to provide methods and a system for a gamma-ray radiography imaging device for medical purposes that serves as an alternative to conventional X-ray imaging systems, which is inexpensive, requires low maintenance, is portable and does not require power.

SUMMARY

In an exemplary embodiment, a gamma radiography system is disclosed. The system includes a gamma source holder; a shaft handle attached at a first end to the gamma source holder; a source container configured to surround the gamma source holder, where the source container is cylindrical; a source container cover attached to a first opening in the source container, where the source container cover is configured to receive and slidingly support the shaft handle; a second opening of the source container, wherein the second opening is configured with threads; a shielded housing having four walls, a floor, and a roof, where the roof includes a threaded opening configured to attach to the threads of the source container; a first wall of the shielded housing including a beam aperture; and an extension connected to the first wall of the shielded housing, such that an opening of the extension covers the beam aperture, wherein the extension includes a plurality of slots each configured to hold a beam modifying device. The shaft handle is configured to move the gamma source holder between a non-deployed position, in which the gamma source holder is surrounded by the source container, to a deployed position, in which the gamma source holder extends from the source container into the shielded housing.

In another exemplary embodiment, a method for using a gamma radiography device is provided. The method includes placing a gamma source material in a gamma source holder, wherein the gamma source holder is attached to a first end of a shaft handle; placing the gamma source holder in a source container; inserting a second end of the shaft handle through a central aperture of a source container cover; screwing threads on the source container to threads of a roof of a shielded housing; installing a handle grip on the second end of the shaft handle; transporting the gamma radiography device to a radiation station; inserting at least one beam modifying device into an extension of the shielded housing; placing the gamma source holder into a deployed position by lowering the shaft handle towards the the shielded housing until the source holder contacts a floor of the shielded housing; keeping the gamma source holder in the deployed position for a desired imaging interval; and placing the gamma source material into a non-deployed position by raising the shaft handle away from the shielded housing until the gamma source holder contacts the source container cover.

In another exemplary embodiment, a method for assembling a gamma radiography device is provided. The method includes welding an extension to a first wall of a shielded housing, wherein the first wall has a beam aperture configured to pass a gamma radiation beam through the extension; attaching a first leg to a first corner of an underside of the shielded housing; attaching a second leg to a second corner of the underside of the shielded housing, wherein the first corner and the second corner are opposite the extension; attaching a third leg to a center of an underside of the extension; installing a caster wheel on an end of each leg; connecting a wheel motor to the caster wheel directly beneath the extension; placing a gamma source holder attached to a shaft handle in a source container such that a grip end of the shaft handle extends through a central aperture of a source container cover; screwing threads on the source container to threads of a roof of the shielded housing; installing a grip on the grip end of the shaft handle; installing a linear motor to the shielded housing and the shaft handle; installing an antenna on an exterior of the shielded housing; installing a controller on the exterior of the shielded housing; and connecting the controller to the antenna, the wheel motor, and the linear motor. The controller is configured to: (a) receive, from a remote control device, direction commands, (b) actuate the wheel motor to transport the gamma radiography system to a radiation station based on the direction commands, (c) receive, from the remote control device, shaft handle direction commands, and (d) actuate the linear motor to one of lower and raise the shaft handle based on the shaft handle direction commands.

The foregoing general description of the illustrative embodiments and the following detailed description thereof are merely exemplary aspects of the teachings of this disclosure, and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
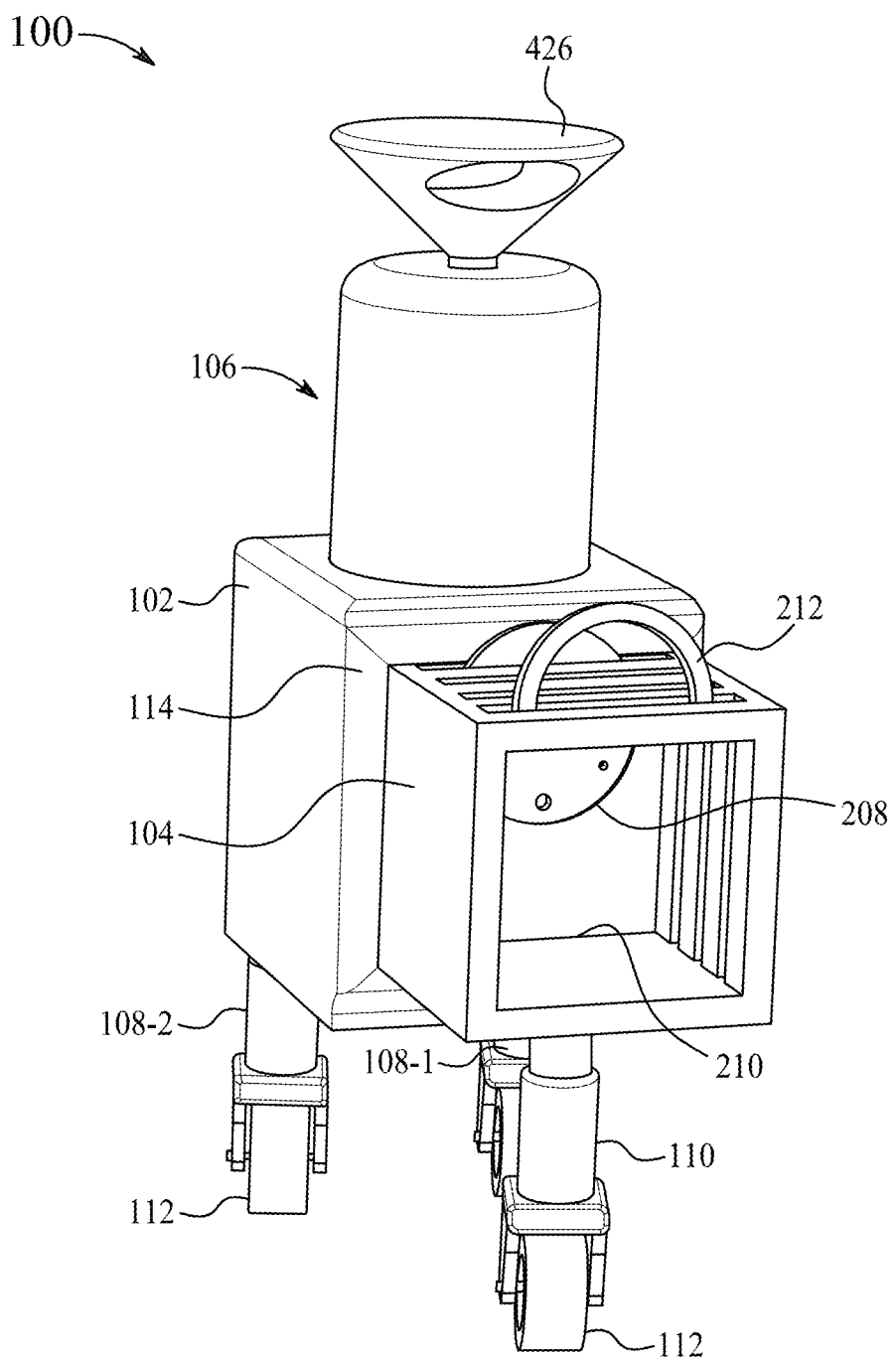
FIG. 1 is a perspective view of a gamma radiography system, according to certain embodiments.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Aspects of the present disclosure are directed to a gamma radiography system, a method for using a gamma radiography device, and a method of assembling the gamma radiography device. The gamma-based imaging system is not bulky as X-ray machines. Additionally, the gamma-based imaging system does not require a high voltage or require high maintenance, and therefore is less expensive, which is important in developing countries. Additionally, the gamma-based imaging system provides acceptable image quality, although not as clear as the diagnostic image quality of an X-ray machine. Such image quality of the gamma-based imaging system may be considered acceptable in cases where an objective of using such system is research work or educational demonstration where high resolution images are not required, or when used in areas that lack electricity.

FIG. 1 illustrates a perspective view of a gamma radiography system 100 (hereinafter referred to as "the system 100"), according to an aspect of the present disclosure. The system 100 includes a shielded housing 102, an extension 104 connected to the shielded housing 102, a source container assembly 106 detachably coupled to the shielded housing 102, a first plurality of legs 108-1, 108-2 connected to an underside of the shielded housing 102, a second plurality of legs 110 connected to the an underside of the extension 104, and a plurality of caster wheels 112 connected to each of the first plurality of legs 108-1, 108-2 and the second plurality of legs 110. According to an aspect, the system 100 is made of stainless steel, weighs 2.8 kg and is inexpensive.

Figure 2:
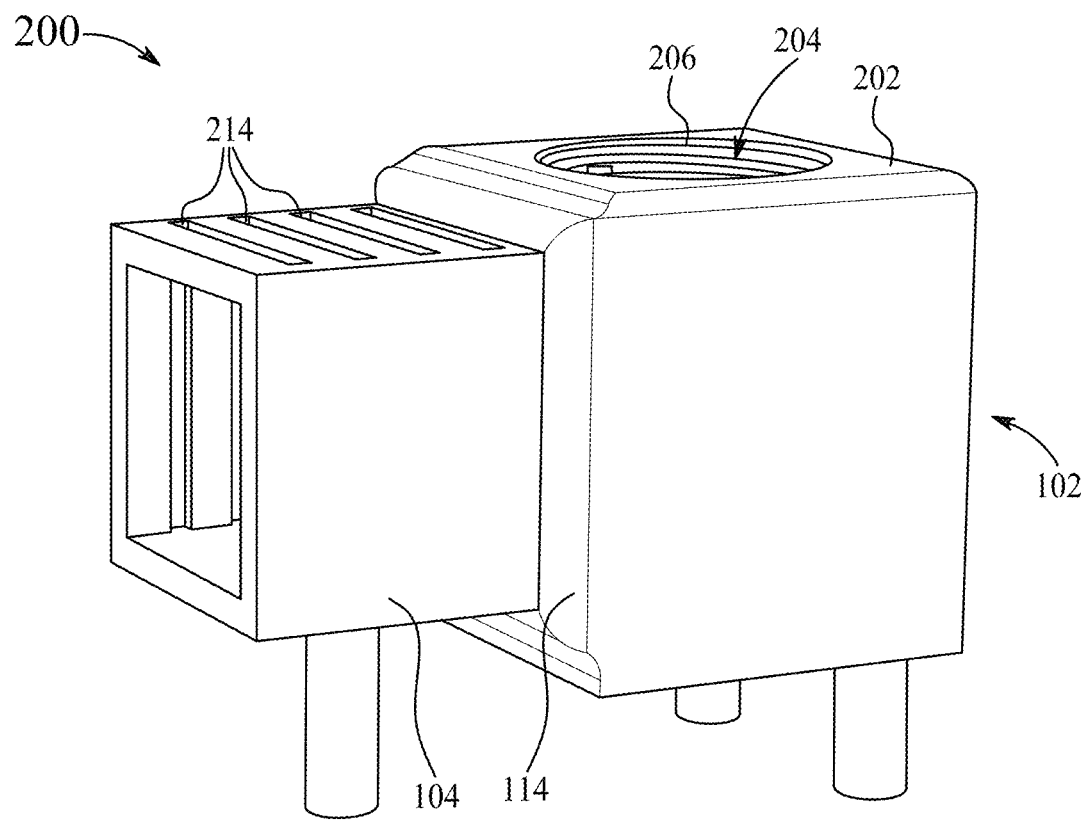
FIG. 2 is a perspective view of a sub-assembly of the gamma radiography system, according to one embodiment.

FIG. 2 illustrates a perspective view of a sub-assembly 200 of the system 100, according to an aspect of the present disclosure. The shielded housing 102 includes four walls, a floor (not shown), and a roof 202. The roof 202 defines an opening 204, where a periphery of the opening 204 includes a first set of threads 206. The shielded housing 102 is made of stainless steel with 2 mm of lead lining in each wall. In some aspects of the present disclosure, the shielded housing 102 has a dimension of 6×6×7 cm$^3$. The extension 104 is connected to a first wall 114 of the shielded housing 102, where the first wall 114 defines a beam aperture 208 (shown in FIG. 1). In some aspects of the present disclosure, the extension 104 has a dimension of 4×5×5 cm$^3$. An opening 210 (shown in FIG. 1) of the extension 104 covers the beam aperture 208. In some aspects of the present disclosure, the opening 210 of the extension 104 is welded to a shielded housing surface which surrounds the beam aperture 208 in the first wall 114 of the shielded housing 102.

Figure 3:
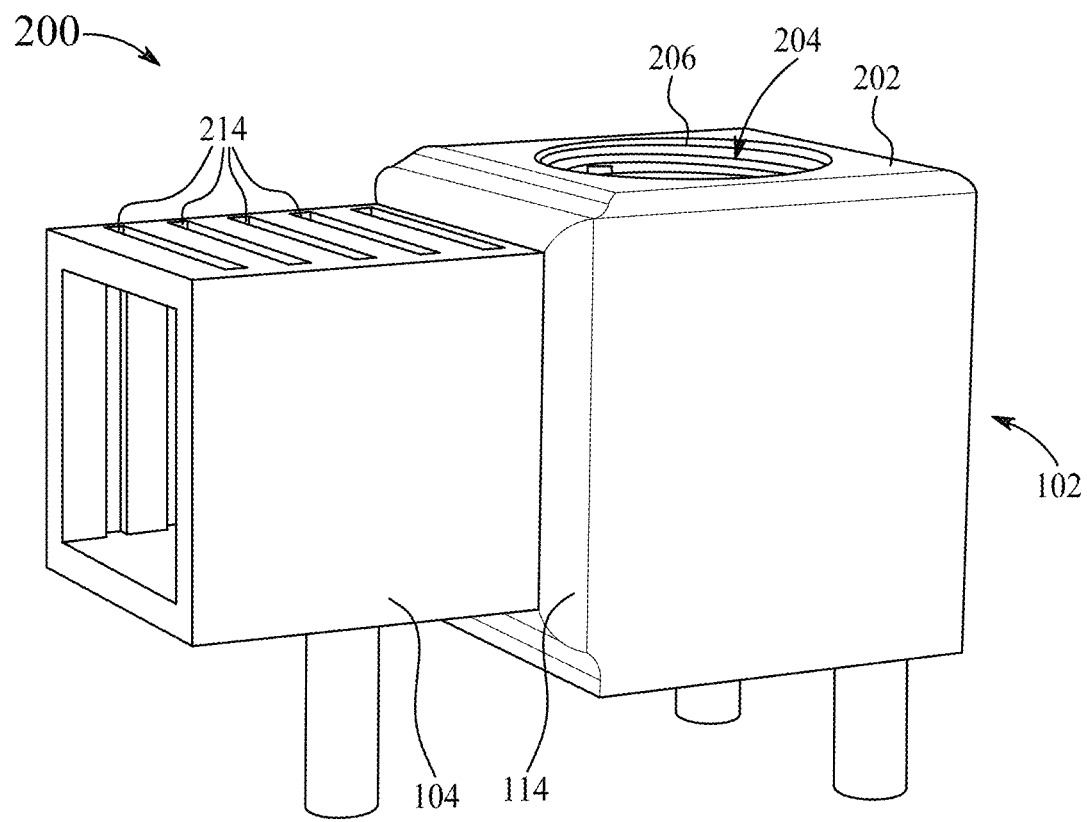
FIG. 3 is a perspective view of the sub-assembly of the gamma radiography system, according to another embodiment.

Further, the extension 104 defines a plurality of slots 214 configured to hold beam modifying devices 212 (shown in FIG. 1). Referring to FIG. 2, the extension 104 defines four slots 214. In some aspects of the present disclosure, as illustrated in FIG. 3, the extension 104 may define five slots 214. However, in other aspects of the present disclosure, the extension 104 may define any number of slots based on quality of imaging to be achieved.

Figure 4:
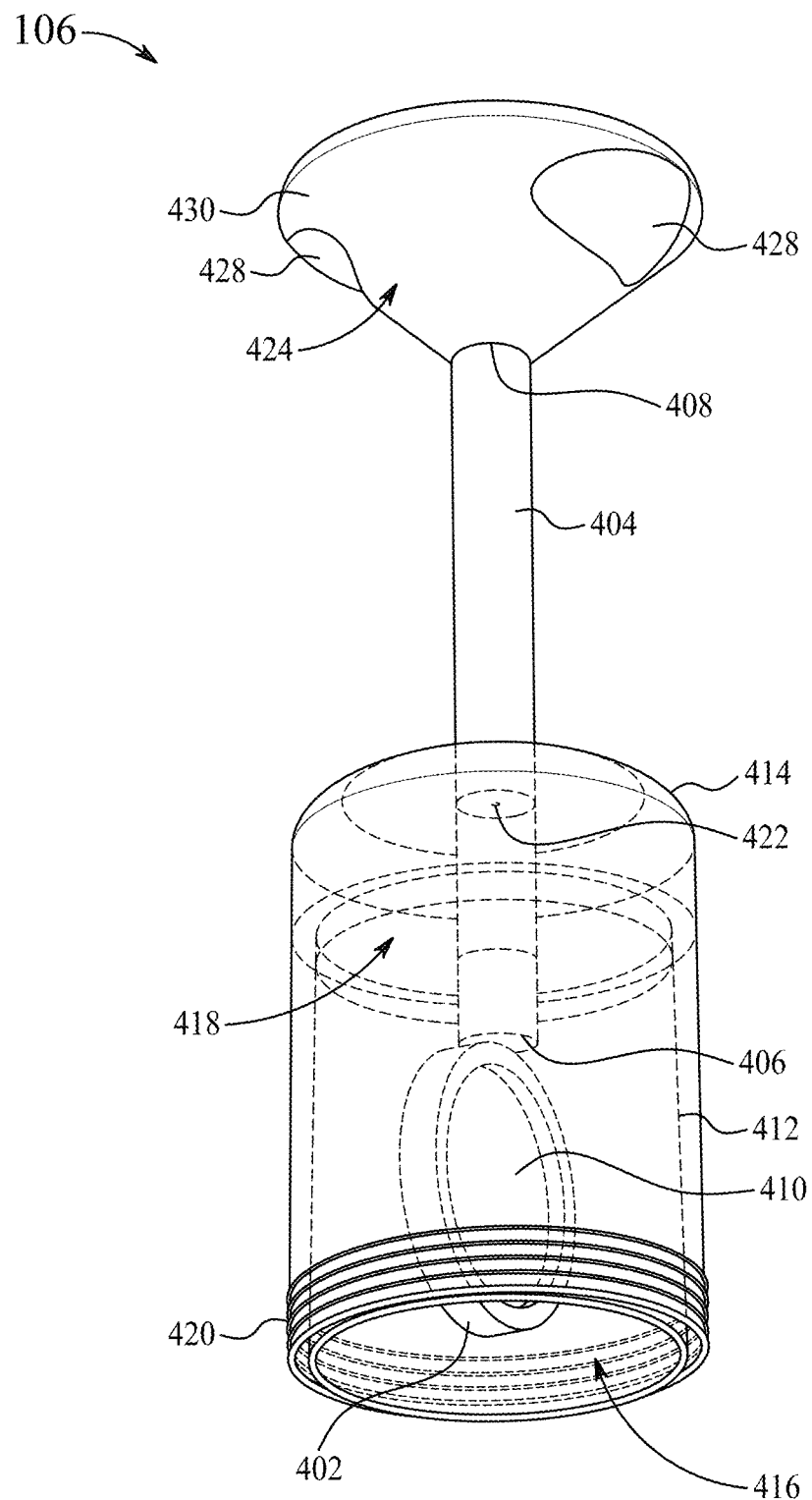
FIG. 4 is a perspective view of a source container assembly of the gamma radiography system, according to certain embodiments.

FIG. 4 illustrates a perspective of the source container assembly 106. The system 100 includes a gamma source holder 402, a shaft handle 404 having a first end 406 and a second end 408, where the first end 406 is attached to the gamma source holder 402. In some embodiments, the system 100 includes a gamma radiation material 410 located within the gamma source holder 402. In a non-limiting example, the gamma radiation material 410 may be selected from a group comprising americium 241, gold 195, cadmium 109, cesium 144, cobalt 57, europium 155, and gadolinium 153. In a non-limiting example, the gamma source holder 402 is configured to hold the gamma radiation material 410 embodied as cylindrical sources having dimensions of 0.4 cm height and 2.5 cm diameter. The shaft handle 404 is made of stainless steel and the gamma source holder 402 is also made of stainless steel with a 1 mm thick lead lining.

The system 100 further includes a source container 412 configured to surround the gamma source holder 402. The source container 412 is a stainless steel cylindrical container with an embedded lead shield to maximize protection when the source container 412 is handled. In a non-limiting example, the embedded lead shield is 3 mm thick. The system 100 further includes a source container cover 414 configured to conceal the source container 412. For example, as seen in FIG. 4, a length and diameter of the source container cover 414 is greater than a length and diameter of the source container 412. As such, the source container cover 414 may circumferentially cover the source container 412 and snugly hold the source container 412 therein. In an example, an inner diameter of the source container cover 414 and an outer diameter of the source container 412 may achieve an interference fit, due to which the source container 412 may be held within the source container cover 414. In a non-limiting example, a thickness of the source container cover 414 is in a range of about 1 centimeter to about 2 centimeters.

Further, the source container 412 defines a first opening 416 at one end of a length thereof and a second opening 418 at an opposite end of the length thereof. In one aspect of the present disclosure, one end of the source container cover 414 circumscribing the second opening 418 of the source container 412 includes a second set of threads 420 configured to engage with the first set of threads 206 of the opening 204 defined in the shielded housing 102. The source container cover 414 is attached to a periphery of the first opening 416 of the source container 412. In such an arrangement, a periphery of the second opening 418 of the source container 412 includes the second set of threads 420 configured to engage with the first set of threads 206. As such, the source container 412 may be detached from the shielded housing 102 in order to replace the gamma radiation material 410. Further, the source container cover 414 is configured to receive and slidingly support the shaft handle 404. The source container cover 414 defines a central aperture 422 configured to receive the shaft handle 404. A diameter of the central aperture 422 is equal to a diameter of the shaft handle 404 plus one millimeter.

In some aspects of the present disclosure, an inner surface of the source container 412, an inner surface of the source container cover 414, and the walls of the shielded housing 102 are lined with a first layer of lead and a second layer of stainless steel, where the second layer of stainless steel covers the first layer of lead.

In some aspects of the present disclosure, a handle grip 424 is attached to the second end 408 of the shaft handle 404. The handle grip 424 is configured with a smooth upper surface 426 (clearly seen in FIG. 1) and indentations 428 within a lower surface 430. The indentations 428 are configured to receive fingers of a user. As such, the user may hold the handle grip 424 with the fingers positioned at the indentations 428 and thereby slide the shaft handle 404 with respect to the source container 412. In some aspects of the present disclosure, the handle grip 424 may be threadably engaged with the second end 408 of the shaft handle 404. As such, in order to change the gamma radiation material 410, the handle grip 424 may be detached from the shaft handle 404 and the gamma source holder 402 may be removed from the source container 412.

To this end, particularly, FIG. 4 illustrates a non-deployed position of the gamma source holder 402, where the gamma source holder 402 is surrounded by the source container 412.

Figure 5:
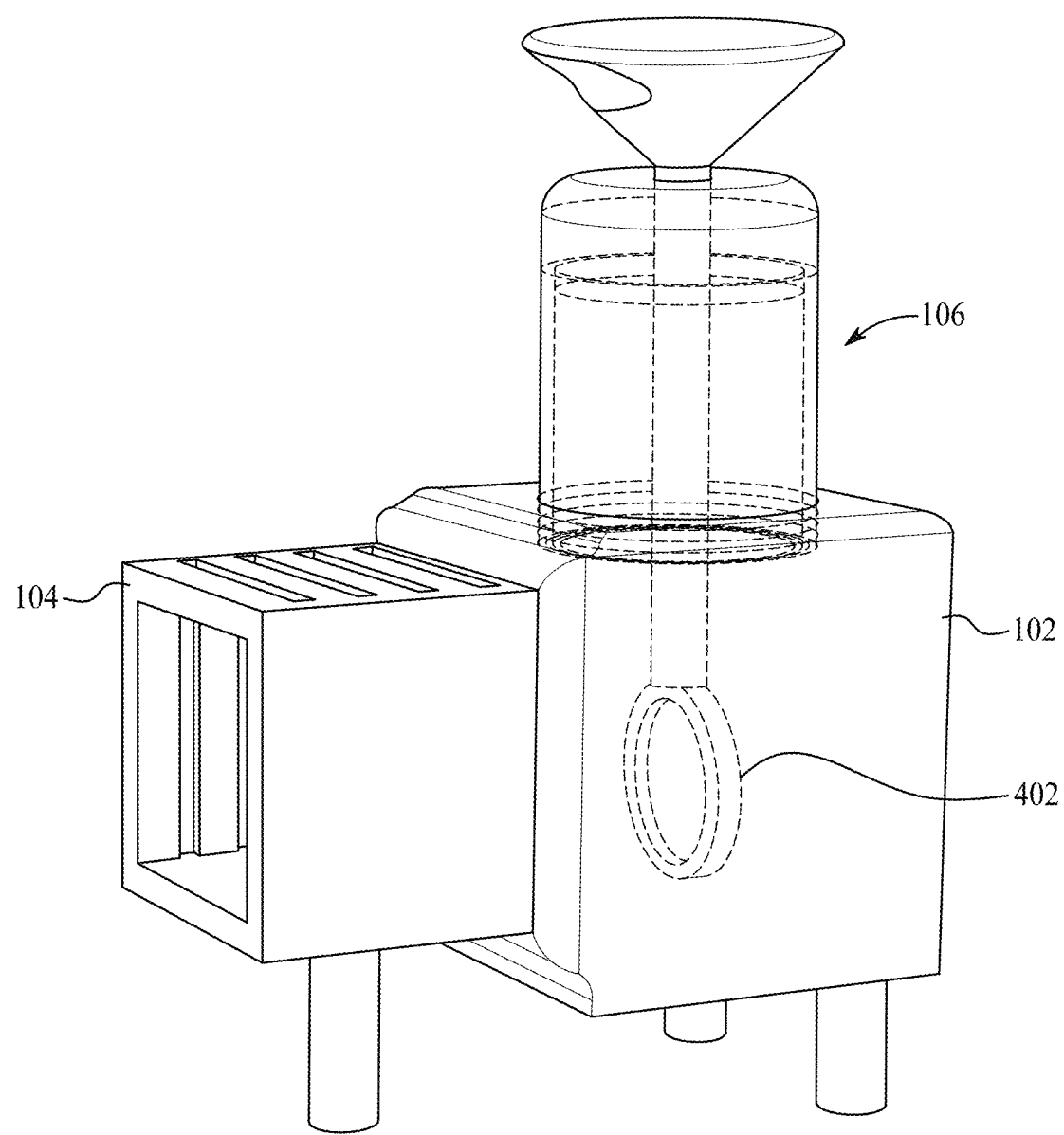
FIG. 5 illustrates a deployed position of a gamma source holder of the gamma radiography system, according to certain embodiments.

FIG. 5 illustrates a deployed position of the gamma source holder 402, where the gamma source holder 402 extends from the source container 412 into the shielded housing 102.

Figure 6:
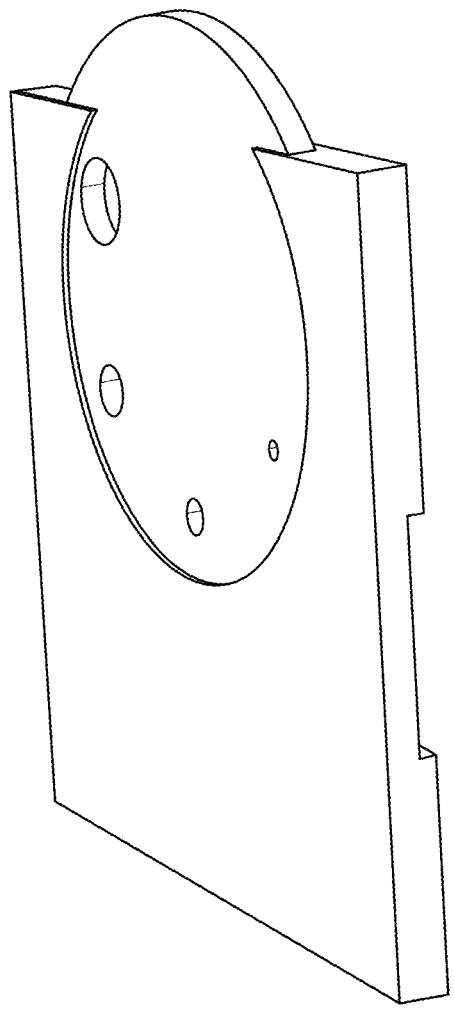
FIG. 6 is a perspective view of a beam modifying device of the gamma radiography system, according to certain embodiments.

FIG. 6 illustrates the beam modifying device 212. In some aspects of the present disclosure, the beam modifying devices 212 are selected from a group comprising collimators and filters. In some aspects of the present disclosure, the beam modifying devices 212 include at least one light filter. In some some aspects of the present disclosures, the beam modifying devices 212 include at least one grating filter.

Figure 7A:
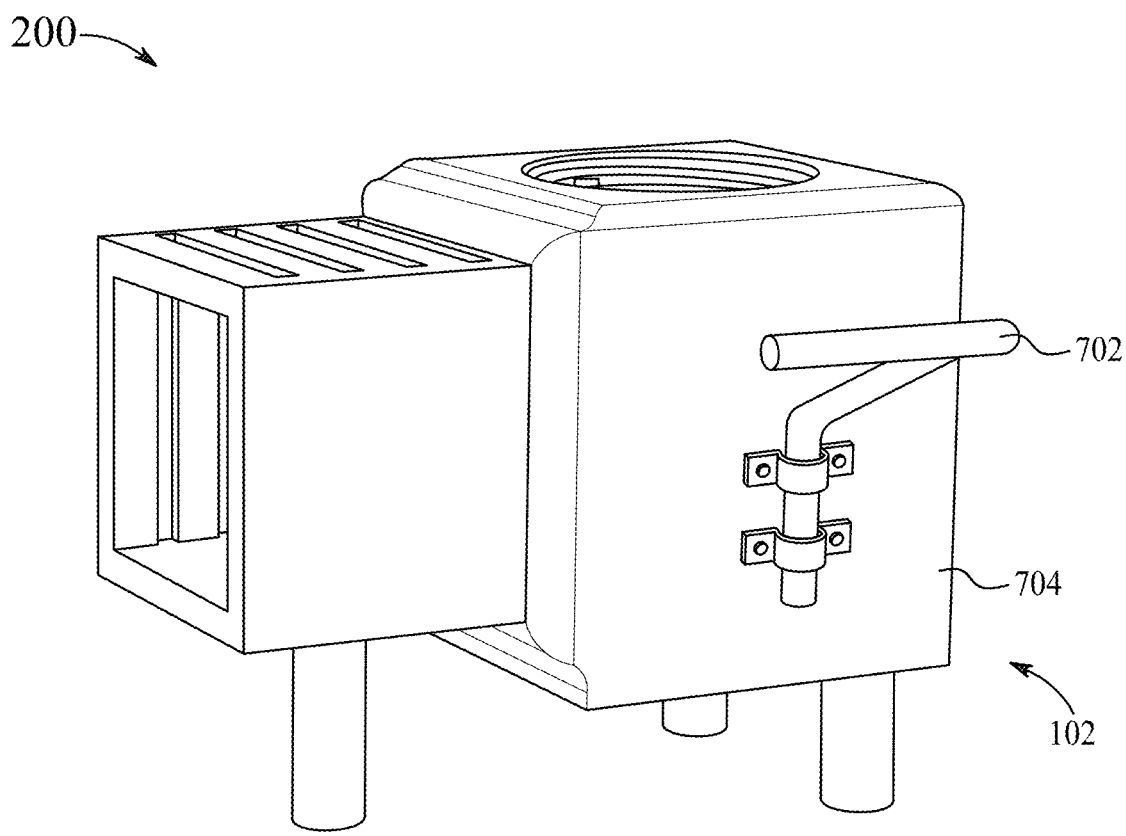
FIG. 7A illustrates a first shielded housing handle of the gamma radiography system, according to certain embodiments.

FIG. 7A illustrates a first shielded housing handle 702, according to an aspect of the present disclosure. The first shielded housing handle 702 is connected to a second wall 704 of the shielded housing 102. In some some aspects of the present disclosure, the first shielded housing handle 702 may be attached to the second wall 704 using one of bolts, rivets, or screws. Although not explicitly illustrated in FIG. 7A, it should be understood that a wall opposite to the second wall 704 includes an identical handle, which, together with the first shielded housing handle 702 helps to lift the system 100.

Figure 7B:
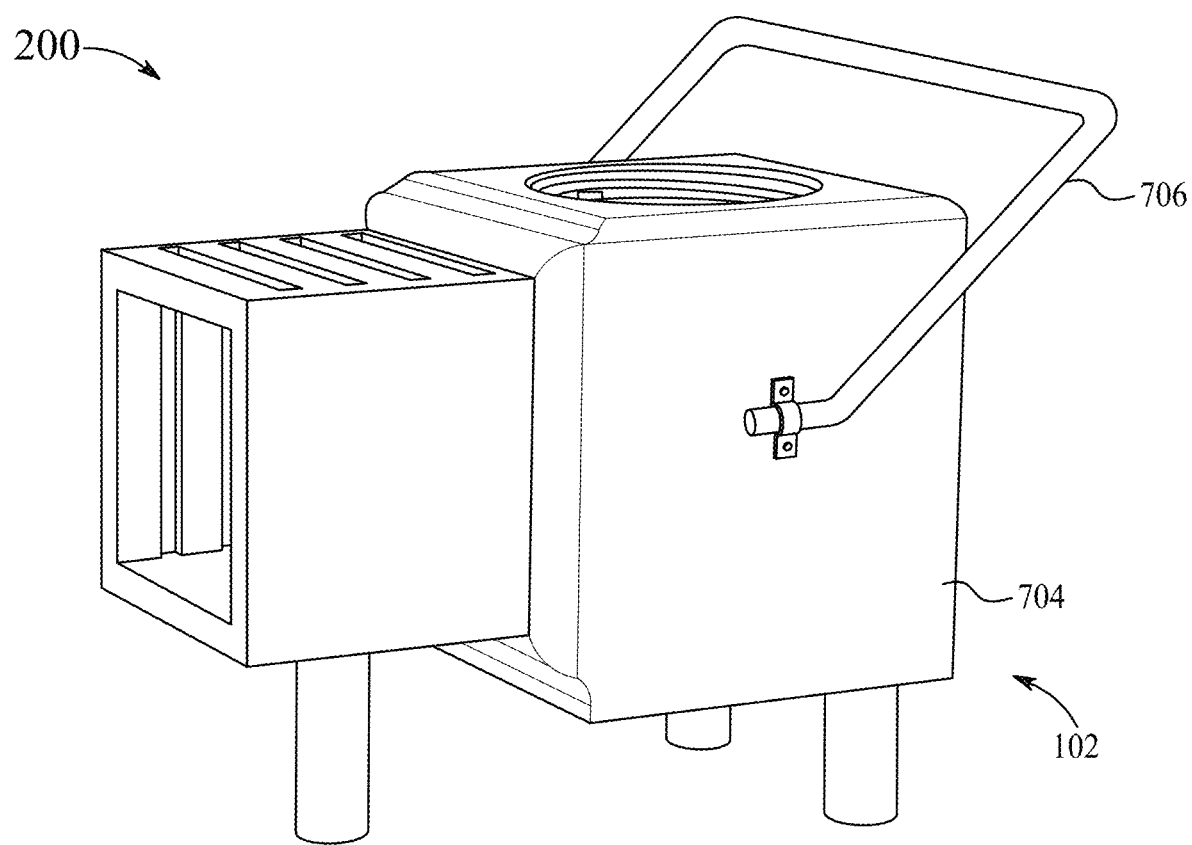
FIG. 7B illustrates a second shielded housing handle of the gamma radiography system, according to certain embodiments.

FIG. 7B illustrates a second shielded housing handle 706, according to another aspect of the present disclosure. Ends of the second shielded housing handle 706 are connected to the second wall 704 and the opposite wall of the shielded housing 102. The second shielded housing handle 706 is used to pull the system 100. The caster wheels are not shown in FIG. 7B, but are understood to be attached to the legs when it is desired to move the gamma radiography system. The first shielded housing handle 702 and the second shielded housing handle 706 are together referred to as "the shielded housing handle" in the present disclosure and are configured to lift and/or pull the shielded housing 102 to and/or from a radiation station.

Figure 8:
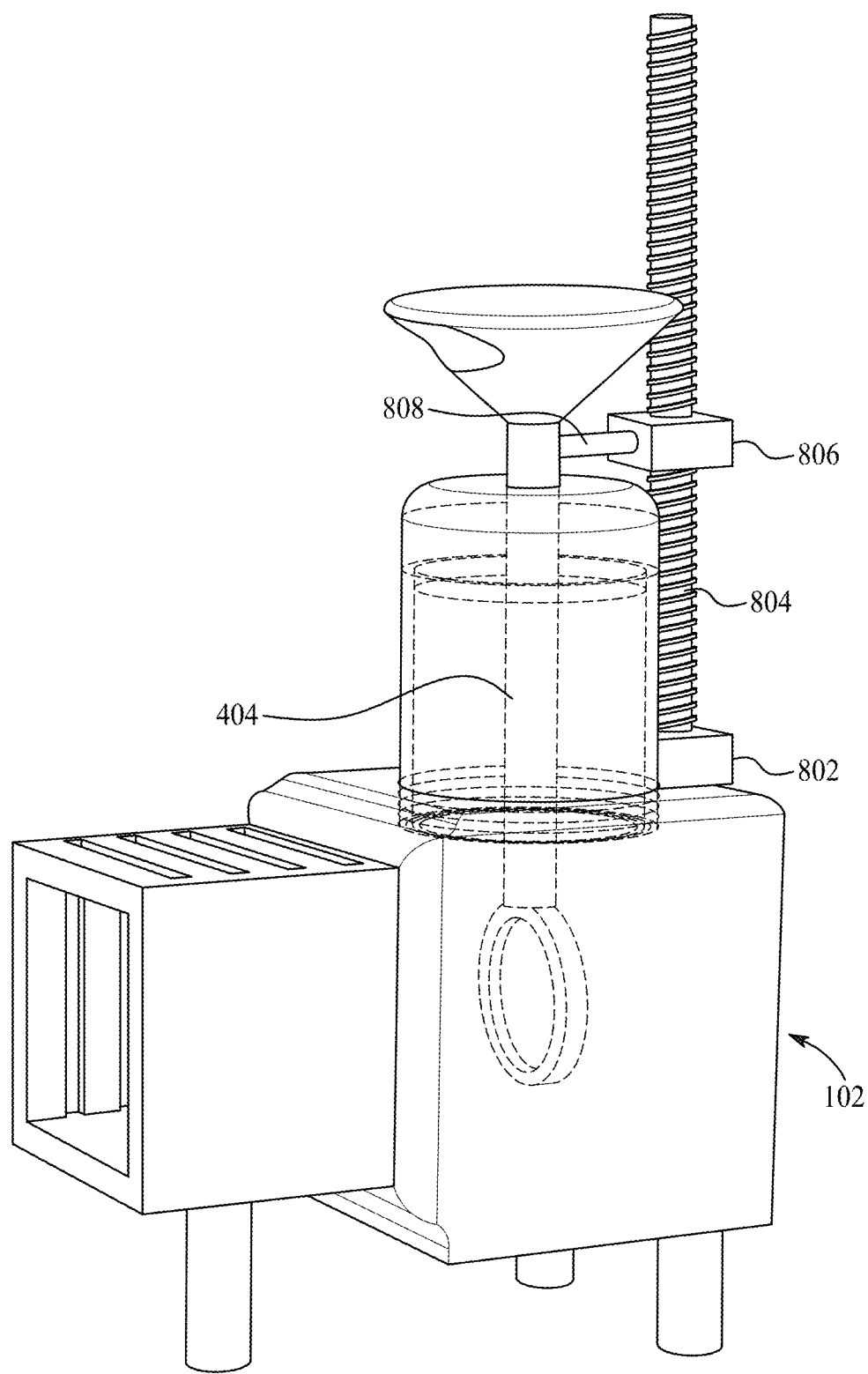
FIG. 8 illustrates a perspective of the gamma radiography system equipped with a linear motor, according to certain embodiments.

FIG. 8 illustrates an aspect of the present disclosure in which a linear actuation mechanism is attached to the shaft handle 404. The linear motor 802 is operatively connected to the shielded housing 102 and the shaft handle 404. The linear motor 802 is configured to raise or lower the shaft handle 404 to move the gamma source holder 402 from the non-deployed position to the deployed position. For example, the linear actuation mechanism includes a screw rod 804 that extends from the linear motor 802, an actuator 806 in threading engagement with the screw rod 806, and a connector 808 extending between the shaft handle 404 and the screw rod 804. When an electrical input of a predefined polarity is supplied to the linear motor 802, the screw rod 804 is allowed to rotate in a direction corresponding to the predefined polarity of the electrical input. Since the actuator 806 is connected to the shaft handle 404 with the connector 808, rotation of the screw rod 804 allows the actuator to move along a length of the screw rod 804, thereby causing movement of the gamma source holder 402 with respect to the shielded housing 102. As such, the gamma source holder 402 may be moved from the non-deployed position to the deployed position. A battery, not shown, may provide the power to operate the linear actuation mechanism. The battery may be a rechargeable battery, which can be recharged when power is available. The gamma radiography system may include both linear motor control and manual control of the shaft handle. In an aspect of the present disclosure, a switch on the surface of the shielded housing may be provided to actuate the linear motor. In another aspect of the present disclosure, the linear motor may be operated wirelessly by a remote control device 906 (see FIG. 9).

Figure 9:
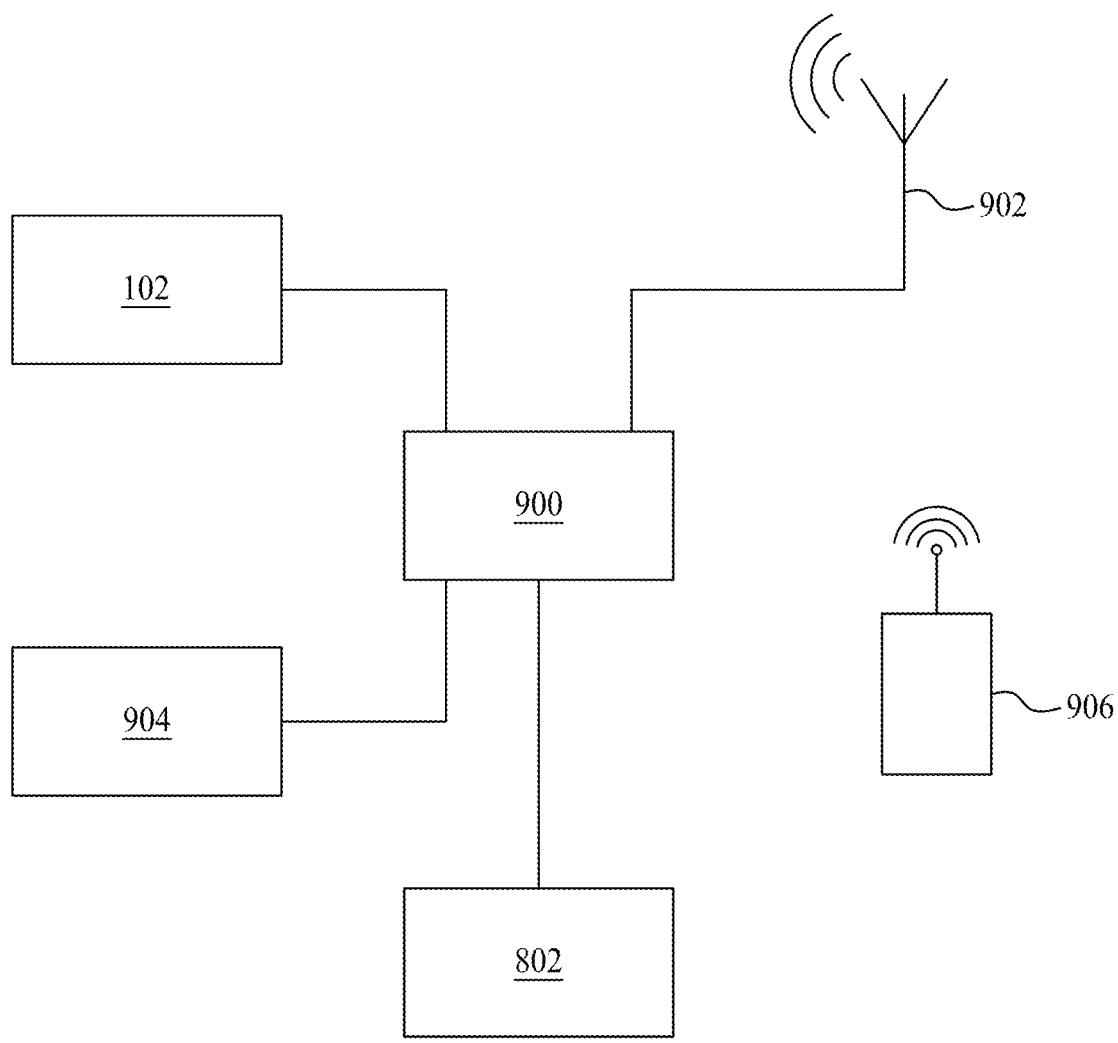
FIG. 9 is a block diagram illustration connections between electrical components of the gamma radiography system, according to certain embodiments.

FIG. 9 illustrates a block diagram of connections between electrical components of the system 100. In an aspect of the present disclosure, the system 100 includes a controller 900 connected to each of the shielded housing 102, an antenna 902, and the plurality of wheel motors 904 attached to the plurality of caster wheels 112. In some aspects, the controller 900 and the antenna 902 may be located on the exterior of the shielded housing 102. A remote control device 906 is communicatively coupled to the antenna 902 and configured to transmit commands to the antenna 902 for actuating the plurality of wheel motors 904. The controller 900 is configured to actuate the plurality of wheel motors 904 to rotate the plurality of caster wheels 112 based on the commands from the remote control device 906. In some aspects, the remote control device 906 is further configured to transmit commands to the antenna 902 for actuating the linear motor 802, where the controller 900 is configured to actuate the linear motor 802 to raise or lower the shaft handle 404 based on the commands from the remote control device 906. As such, the user may operate the system 100 from a remote location.

Figure 10:
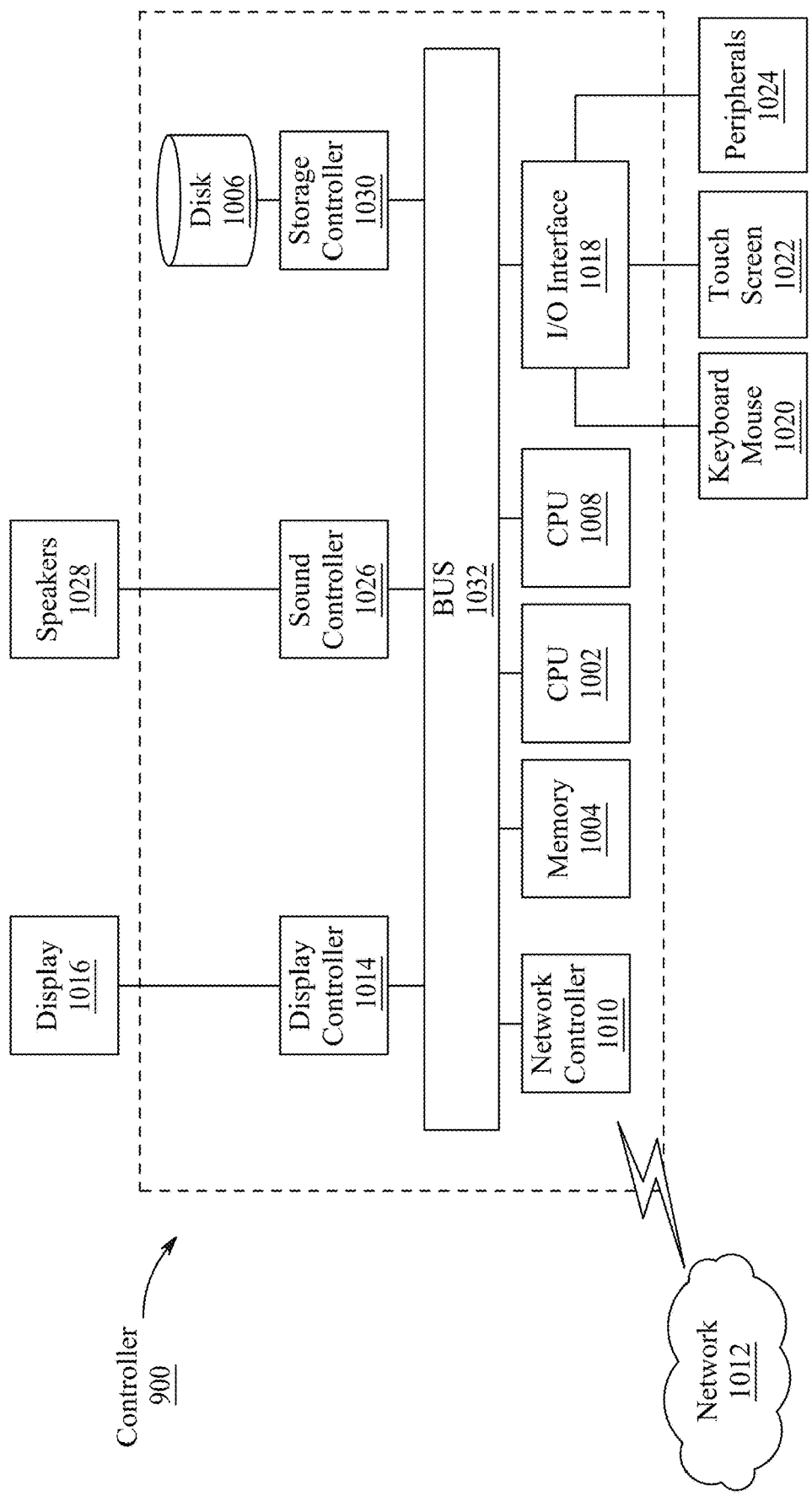
FIG. 10 is an illustration of a non-limiting example of details of computing hardware used in the computing system, according to certain embodiments.

Next, further details of the hardware description of the computing environment according to exemplary embodiments is described with reference to FIG. 10. In FIG. 10, the controller 900 is embodied as a computing device which includes a CPU 1002 which performs the processes described above/below. The process data and instructions may be stored in memory 1004. These processes and instructions may also be stored on a storage medium disk 1006 such as a hard drive (HDD) or portable storage medium or may be stored remotely.

Further, the claims are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computing device communicates, such as a server or computer.

Further, the claims may be provided as a utility application, background daemon, or component of an operating system, or combination thereof, executing in conjunction with the CPU 1002, 1008 and an operating system such as Microsoft Windows 7, Microsoft Windows 10, Microsoft Windows 11, UNIX, Solaris, LINUX, Apple MAC-OS and other systems known to those skilled in the art.

The hardware elements in order to achieve the computing device may be realized by various circuitry elements, known to those skilled in the art. For example, the CPU 1002 or 1008 may be a Xenon or Core processor from Intel of America or an Opteron processor from AMD of America, or may be other processor types that would be recognized by one of ordinary skill in the art. Alternatively, the CPU 1002, 1008 may be implemented on an FPGA, ASIC, PLD or using discrete logic circuits, as one of ordinary skill in the art would recognize. Further, the CPU 1002, 1008 may be implemented as multiple processors cooperatively working in parallel to perform the instructions of the inventive processes described above.

The computing device in FIG. 10 also includes a network controller 1010, such as an Intel Ethernet PRO network interface card from Intel Corporation of America, for interfacing with a network 1012. As can be appreciated, the network 1012 can be a public network, such as the Internet, or a private network such as an LAN or WAN network, or any combination thereof and can also include PSTN or ISDN sub-networks. The network 1012 can also be wired, such as an Ethernet network, or can be wireless such as a cellular network including EDGE, 3G, 4G and 5G wireless cellular systems. The wireless network can also be WiFi, Bluetooth, or any other wireless form of communication that is known.

The computing device further includes a display controller 1014, such as a NVIDIA GeForce GTX or Quadro graphics adaptor from NVIDIA Corporation of America for interfacing with a display 1016, such as a Hewlett Packard HPL2445w LCD monitor. A general purpose I/O interface 1018 interfaces with a keyboard and/or mouse 1020 as well as a touch screen panel 1022 on or separate from the display 1016. The general purpose I/O interface 1018 also connects to a variety of peripherals 1024 including printers and scanners, such as an OfficeJet or DeskJet from Hewlett Packard.

A sound controller 1026 is also provided in the computing device such as Sound Blaster X-Fi Titanium from Creative, to interface with speakers/microphone 1028 thereby providing sounds and/or music.

A general purpose storage controller 1030 connects the storage medium disk 1006 with a communication bus 1032, which may be an ISA, EISA, VESA, PCI, or similar, for interconnecting all of the components of the computing device. A description of the general features and functionality of the display 1016, the keyboard and/or mouse 1020, as well as the display controller 1014, the storage controller 1030, the network controller 1010, the sound controller 1026, and the general purpose I/O interface 1018 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset. The above-described hardware description is a non-limiting example of corresponding structure for performing the functionality described herein.

Figure 11:
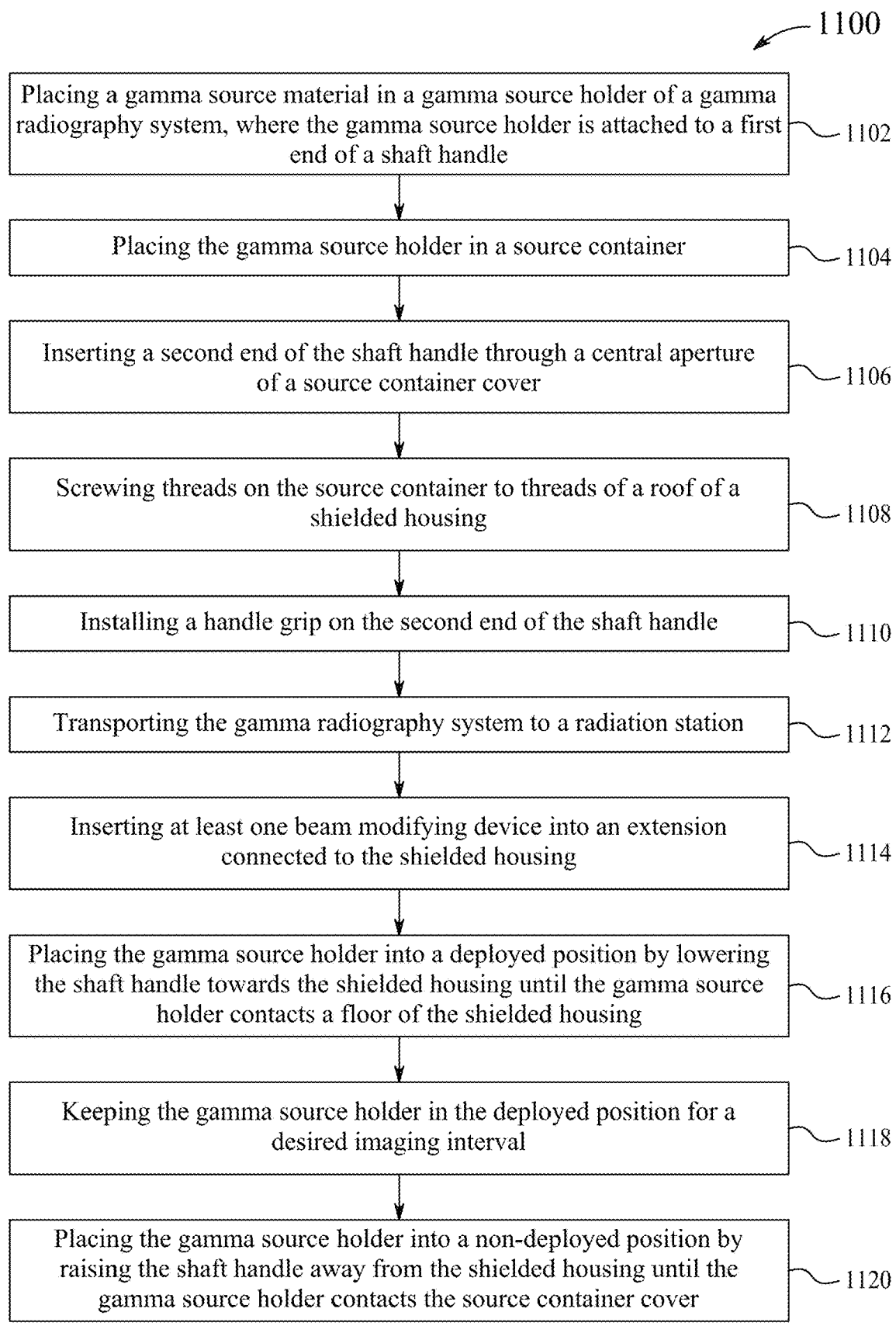
FIG. 11 is a flowchart of a method for using the gamma radiography system, according to certain embodiments.

FIG. 11 illustrates a flowchart of a method 1100 for using the system 100. The method 1100 is described with reference to FIG. 1 through FIG. 9. At step 1102, the method 1100 includes placing the gamma source material 410 in the gamma source holder 402, where the gamma source holder 402 is attached to the first end 406 of the shaft handle 404.

At step 1104, the method 1100 includes placing the gamma source holder 402 in the source container 412

At step 1106, the method 1100 includes inserting the second end 408 of the shaft handle 404 through the central aperture 422 of the source container cover 414.

At step 1108, the method 1100 includes screwing threads 420 on the source container 412 to threads 206 of the roof 202 of the shielded housing 102.

At step 1110, the method 1100 includes installing the handle grip 424 on the second end 408 of the shaft handle 404.

At step 1112, the method 1100 includes transporting the gamma radiography system 100 to a radiation station. In one embodiments, the step of transporting includes transmitting, via the remote control device 906, direction commands; receiving, by the antenna 902 coupled to the controller 900, the direction commands; and actuating, by the controller 900, the plurality of wheel motors 904 connected to the plurality of caster wheels 112 of the system 100 until the system 100 docks into the radiation station. In another embodiment, the step of transporting includes performing one or more of lifting and pulling, by the shielded housing handle 702, 706, the system 100 to the radiation station.

At step 1114, the method 1100 includes inserting at least one beam modifying device 212 into the extension 104 connected to the shielded housing 102.

At step 1116, the method 1100 includes placing the gamma source holder 402 into the deployed position by lowering the shaft handle 404 towards the shielded housing 102 until the gamma source holder 402 contacts the floor of the shielded housing 102.

At step 1118, the method 1100 includes keeping the gamma source holder 402 in the deployed position for a desired imaging interval.

At step 1120, the method 1100 includes placing the gamma source holder 402 into the non-deployed position by raising the shaft handle 404 away from the shielded housing 102 until the gamma source holder 402 contacts the source container cover 414. In one aspect, the step of placing the gamma source holder 402 into one of the deployed position and the non-deployed position includes transmitting, with the remote control device 906, the shaft handle direction commands; receiving, by the antenna 902 coupled to the controller 900, the shaft handle direction commands; actuating, by the controller 900, the linear motor 802 connected to the shielded housing 102 and the shaft handle 404 to one of lower and raise the shaft handle 404.

According to another aspect of the present disclosure, a method for assembling the system 100 is provided. The method includes welding the extension 104 to the first wall 114 of the shielded housing 102, where the first wall 102 defines the beam aperture 208 configured to pass a gamma radiation beam through the extension 104; attaching the first leg 108-1 to a first corner and a second leg 108-2 to a second corner of an underside of the shielded housing 102; attaching a third leg 110 to a center of an underside of the extension 104; installing the caster wheel 112 on an end of each leg; connecting the wheel motor 904 to the caster wheel 112 directly beneath the extension 104; placing the gamma source holder 402 attached to the shaft handle 404 in the source container 412 such that a grip end (second end 408) of the shaft handle 404 extends through the central aperture 422 of the source container cover 414; screwing threads 420 on the source container 412 to threads 206 of the roof 202 of the shielded housing 102; installing the handle grip 424 on the grip end 408 of the shaft handle 404; installing the linear motor 802 to the shielded housing 102 and the shaft handle 404; installing the antenna 902 and the controller 900 on an exterior of the shielded housing 102; connecting the controller 900 to the antenna 902, the wheel motor 904, and the linear motor 802. The controller 900 is configured to (a) receive direction commands from the remote control device 906, (b) actuate the wheel motor 904 to transport the system 100 to the radiation station based on the direction commands, (c) receive shaft handle direction commands from the remote control device 906, (d) actuate the linear motor 802 to one of lower and raise the shaft handle 404 based on the shaft handle direction commands.

Figure 12A:
FIG. 12A is a radiography image of humanoid phantoms obtained using 1 Ci cylindrically-shaped source with 3 cm in diameter, according to an aspect of the present disclosure.
Figure 12B:
FIG. 12B is a radiography image of humanoid phantoms obtained using 1 mCi source with approximately 2 mm in diameter and 3 mm in height, according to an aspect of the present disclosure.
Figure 12C:
FIG. 12C is a radiography image of humanoid phantoms obtained using an X-ray machine, according to an aspect of the present disclosure.

FIGS. 12A, 12B, and 12C illustrate images of a humanoid phantom obtained using three Am-241 sources. Particularly, FIG. 12A is an image obtained using 1 Ci cylindrically-shaped source with 3 cm in diameter, FIG. 12B is an image obtained using 1 mCi source with approximately 2 mm in diameter and 3 mm in height, and FIG. 12C is an image obtained using a an X ray machine. All three sources were used to acquire an image at a SID of 35 cm using a computed radiography imaging plate with a pixel size of 0.08 mm. Images obtained with the 1 Ci source at different times showed poor sharpness. The addition of 2 mm lead sheets with circular 0.5-4 mm openings improved the image quality slightly. The main advantage of using the 1 Ci source was its high activity which shortened the acquisition time to 10 seconds when no lead sheets were used. The 1 mCi source produced superior quality images with imaging times 8-10 hours, as illustrated in FIG. 12B. For given dimensions of the source, the expected activity $A_E$ can be calculated as follows:

$$A_E = A_S \times V \times \rho = 3.5 Ci/g \times 0.3 \text{ cm} \times \pi \times 0.1^2 \text{ cm}^2 \times 12 \text{ g/cm}^3 = 395 mCi$$

where $A_S$ is the specific activity, V is the source volume and $\rho$ is the source density.

The expected activity was approximately 400 times the effective activity of the source, which indicate that the source was non-pure. Consequently, using a pure Am-241 source with the same dimensions may reduce the time significantly. Among sources considered feasible, Am-241 is the lowest in terms of specific activity and among the lowest in terms of useful beam output per curie (2nd lowest after Ce-144). As a result, the other sources, except for Ce-144, should have higher useful radiation output per the same source size. Activity corresponding to the same source size for the other radionuclides is presented in Table-1.

| Nuclide | Half life | Density (g/cm$^3$) | S. Activity (Ci/g) | Activity for 3 × 2 mm cylindrical source (Ci) |
|---|---|---|---|---|
| Am-241 | 432.2 y | 12.0 | 3.50 | 0.39 |
| Au-195 | 186.01 d | 19.32 | 3598.62 | 655.26 |
| Cd-109 | 461.9 d | 8.7 | 2592.58 | 212.58 |
| Ce-144 | 284.91 d | 6.76 | 3181.53 | 202.70 |
| Co-57 | 271.79 d | 8.9 | 8405.36 | 705.05 |
| Eu-155 | 4.7611 y | 5.25 | 483.43 | 23.92 |
| Gd-153 | 240.4 d | 7.9 | 3540.29 | 263.59 |

Table-1. List of feasible gamma sources along with their specific activity, density and activity corresponding to a cylindrical source of 2 mm height and 3 mm diameter The activity shown in Table-1 is calculated for pure sources and does not represent the effective activity for each source. Each source has a self-absorption, which reduces the number of emissions leaving the source volume. This effect, however, should not have a major impact on the source activity, given the relatively small source size and the energies of the emitted photons.

Sources having key desired characteristics were simulated using the Monte Carlo toolkit GATE 9.0. The aim of these simulations was to simplify the emission spectra, making it easier to assess the source feasibility. Emission spectrums were obtained by simulating 1 GBq (Giga Becquerel) activity for 1 second and detecting all emitted gamma. Then, the spectrum of each source was analyzed to find the total number of photons with energies within and outside the diagnostic range. Photons outside the diagnostic range were further classified as below the range, higher than the range (125-300 keV) and significantly higher than the range (>300 keV). Photons below the diagnostic range have a high absorption probability; and therefore, they contribute to the patient dose while providing no diagnostically useful information. A filter was added to remove most of these photons, but the filter would also remove some of the useful photons.

Photons above the diagnostic range may contribute, depending on the energy, to both image formation and dose. In terms of image quality, Compton scattering becomes more dominant as energy increases; therefore, these high energy photons reduce image contrast. As for the radiation dose, increasing the energy reduces absorption probability, and most of the absorbed dose results from Compton interaction. For such sources to be considered feasible, their dose contribution need to be insignificant, and the image quality must remain within acceptable limits. Additionally, sources with high energy photons may significantly increase the shielding requirement if their emission probability is relatively high.

After analysis, sources with spectra that meet one of the following characteristics were excluded:
- Any source with the highest energy peak occurring above the diagnostic range.
- Any source with the highest energy peak occurring below the diagnostic range.
- Any source where the total photons intensity in the diagnostic range is approximately equal or significantly less than the total intensity outside the diagnostic range.

Sources mentioned above were considered impractical as they would require either heavy filtering to remove low energy photons and/or they could increase the shielding requirements of the system significantly. The remaining sources are shown in Table-2. The percentages represent the number of emissions within an energy range per disintegration (e.g., 1 photon emitted per 10 disintegrations=10%). Examples of sources excluded are presented in Table-3.

TABLE 2

List of energy-feasible sources

| Nuclide | <20 keV | 20-140 keV | 140-300 keV | >300 keV |
|---|---|---|---|---|
| Am-243 | 0.03% | 74.08% | 0.15% | 0.00% |
| Am-241 | 0.00% | 38.61% | 0.00% | 0.00% |
| Au-195 | 25.25% | 49.82% | 0.02% | 0.00% |
| Cd-109 | 25.25% | 49.82% | 0.02% | 0.00% |
| Ce-144 | 0.00% | 13.00% | 0.00% | 1.47% |
| Co-57 | 39.77% | 96.37% | 0.00% | 0.18% |
| Dy-159 | 16.56% | 77.39% | 0.00% | 0.00% |
| Eu-155 | 0.05% | 54.97% | 0.05% | 0.00% |
| Gd-153 | 15.08% | 128.29% | 0.04% | 0.00% |
| La-137 | 10.09% | 75.95% | 0.00% | 0.00% |
| Np-237 | 0.01% | 35.23% | 2.42% | 0.00% |
| Pm-143 | 12.74% | 76.44% | 0.00% | 38.56% |
| Pm-145 | 12.51% | 71.55% | 0.00% | 0.00% |
| Sm-145 | 20.54% | 129.27% | 0.00% | 0.00% |
| Sn-113 | 6.62% | 73.33% | 2.11% | 32.26% |
| Ta-179 | 18.16% | 43.96% | 0.00% | 0.00% |
| Ti-44 | 17.23% | 125.43% | 0.06% | 61.11% |
| W-181 | 22.16% | 65.02% | 0.01% | 0.00% |

TABLE 3

Example of excluded sources

| Nuclide | <20 keV | 20-140 keV | 140-300 keV | >300 keV | Exclusion Reason |
|---|---|---|---|---|---|
| Ba-133 | 9.159% | 99.741% | 8.216% | 89.148% | High non-diagnostic range energy emission |
| Eu-152 | 10.277% | 83.523% | 8.226% | 122.050% | High non-diagnostic range energy emission |
| Hf-172 | 35.713% | 183.490% | 25.474% | 150.130% | High non-diagnostic range energy emission |
| Hg-197 | 31.778% | 92.311% | 0.677% | 0.000% | Short half-life |
| I-125 | 7.945% | 77.010% | 0.000% | 0.000% | Short half-life |
| Ta-182 | 0.000% | 66.180% | 29.158% | 99.493% | High non-diagnostic range energy emission |
| Tb-155 | 15.846% | 138.040% | 28.395% | 3.992% | Short half-life |

As the source size increases, both the activity and geometric un-sharpness increases. Higher activity corresponds to shorter image acquisition time and, therefore, less patient discomfort and motion artifacts. However, in some cases, a longer acquisition time might be acceptable to some extent. For instance, in studies where phantoms are used, patient movement and discomfort are not of concern. Therefore, acquisition time can be considered application-dependent. Geometric un-sharpness can be reduced by either using a smaller source size or increasing the source-to-image distance (SID) (See: Bushberg, J. T., Seibert, J. A., Leidholdt, E. M., Boone, J. M., Goldschmidt, E. J., 2012. The Essential Physics of Medical Imaging, 3rd ed, Medical Physics). As a result, a longer image acquisition time would be required. The size of the source must be small enough to preserve sharpness and large enough to keep the acquisition time within an acceptable limit.

Another desired characteristic for imaging sources is high specific activity. Sources with high specific activity emit more activity per gram; therefore, they can be small and have high activity. However, sources with higher specific activity tend to have a lower half-life, as can be deduced from Table-1. Sources with a lower half-life would require more frequent replacement as the source output would decrease with time. The specific activity for each nuclide was calculated using the following equation:

$$A_s = \frac{\ln(2) \times N_{Av}}{t_{1/2} \times M}$$

where, $N_{Av}$ is Avogadro's number and $A_S$, $t_{1/2}$, and M are the specific activity, half-life, and atomic mass of the radionuclide, respectively (See: Kratz, J.-V., Lieser, K. H. (Eds.), 2013. Nuclear and Radiochemistry. Wiley-VCH Verlag GmbH & Co. KGaA, Weinheim, Germany).

An objective of shielding any radioactive source is to reduce the received dose to acceptable levels. Generally, the exposure from the imaging system can occur when the system is being used or when it is in the off position. Either way, the dose should not exceed 1 mSv/year to the public and 20 mSv/year (Sievert/yr) for the radiation worker (See: Johnson, T. E., 2017. Introduction to Health Physics, Fifth Edition. McGraw-Hill Education).

Members of the public are not expected to stay in close proximity of the system 100. When the system 100 was kept within an enclosed, restricted, or controlled area next to an uncontrolled fully occupied area, the area walls and a distance between the source and walls would significantly reduce exposure. However, during transporting the system 100, members of the public might remain in close proximity of the system 100 for some time. For example, members of the public may be in close proximity when the system 100 is being moved through narrow corridors.

Patients have no dose limit. However, the dose to patients should be kept as low as reasonably achievable. Leakage radiation is an example of unnecessary dose. Radiation leaking from the shielded housing 102 provides unnecessary dose to the patient and might reduce the image quality. According to the National Committee of Radiation Protection (NCRP), leakage radiation air kerma must not exceed 1 mGy (milligray) in 1 hour at 1 m meter distance for diagnostic X-ray tubes. An equivalent dose in milliSievert (mSv) is equal to an absorbed dose in mGy. An amount of shielding needed is dependent on source energy and activity. Instead of designing a shield suited for each application/source combination, it was observed that having a universal shield that can be used with any feasible source was convenient.

Each feasible source emits multiple energies with different emission rates. The gamma-specific-ray constant is a metric that can indicate the strength of a source. Therefore, it can be used to find the source with the highest strength among feasible sources. Then, it can be assumed that any shield satisfying the dose limit target for that source would fulfill it for all other feasible sources. Among all feasible sources, Gd-153 has the highest specific gamma-ray constant (See: Peplow, D. E., 2020. Specific Gamma-Ray Dose Constants with Current Emission Data. Health Phys. 118, 402-416).

An exposure time of 8-10 hours was required to produce an acceptable image with Am-241 1 mCi source. Increasing the source activity to 1 Ci (Curie-1 Ci=$3.7 \times 10^{10}$ Bq) would reduce the exposure time to less than a minute. Considering that most sources have greater useful beam output per curie than Am-241, it is reasonable to deduce that sources with activities up to 10 Ci would be sufficient to produce acceptable images for various radiological procedures in a reasonable acquisition time. Accordingly, the shielding of the system 100 was designed to reduce the dose received from 10 Ci of Gd-153 to the acceptable limits.

The required shielding was estimated by simulating a Gd-153 isotropic point source for 1 second. A shield was placed around the source and its material and thickness was varied. The dose was measured at the inner surface of the shield, outer surface of the shield and at 1 m distance from the source. Three materials were considered as shields: tungsten, lead, and stainless steel.

Figure 13A:
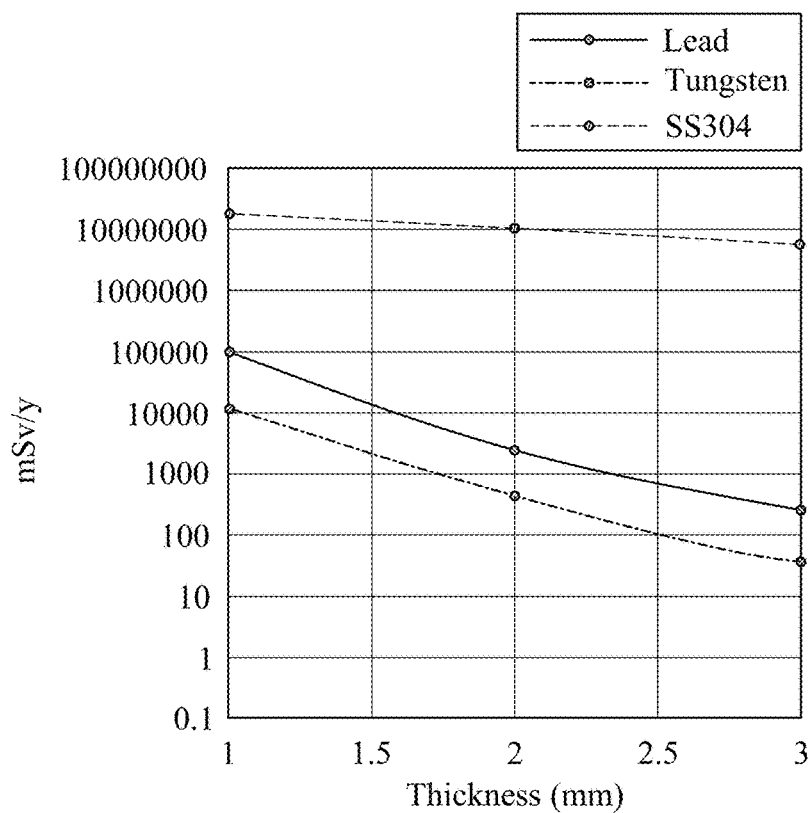
FIG. 13A is a graph illustrating variation is dose received from Gd-153 at the surface of the shield for various shielding thicknesses and materials, according to an aspect of the present disclosure.
Figure 13B:
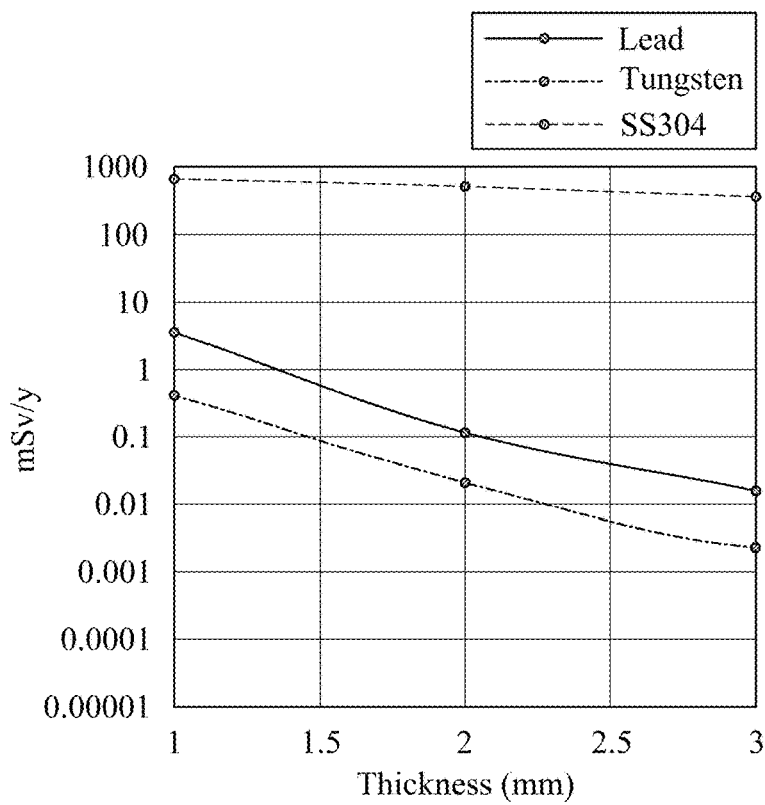
FIG. 13B is a graph illustrating variation is dose received from Gd-153 at a distance of 1 m for various shielding thicknesses and materials, according to an aspect of the present disclosure.

FIG. 13A is a graph illustrating variation of dose received from Gd-153 at the surface of the shield for various shielding thicknesses and materials, and FIG. 13B is a graph illustrating variation of dose received from Gd-153 at a distance of 1 m for various shielding thicknesses and materials. From the graphs, it may be observed that the dose can be kept below 20 mSv/year by using either ~1 mm of tungsten or ~2 mm of lead as the shield. These thicknesses also keep the dose at 1 m below 1 mGy/hr. These dose values are obtained assuming that a working year is 2000 hours. It should also be noted that these values reflect on the dose that will be accumulated if a person is in close contact with the source for 8 hours per day in a year.

Tungsten is shown to require less material than lead to reduce the dose to the acceptable limit. However, tungsten is more expensive and heavier. Lead, on the other hand, is toxic and not self-supporting. Stainless steel is the least expensive, but is less effective as a shield. Considering the high cost of tungsten compared to lead and the comparable shielding efficiency, lead was preferred as a shield for the system. To overcome the self-support issue, the lead 2 mm shield is placed between two stainless-steel plates to provide support, protection for the shield, facilitate handling of the system and also serve as an additional shielding.

The system 100 was modeled in GATE to estimate the dose distribution within and around the system for 10 Ci of Gd-153. GATE utilizes tools known as actors to collect interaction and dosimetric information in simulations. A dose actor was attached to the system 100. The dose actor creates a dose map depending on the number and size of voxels selected. The dose map consisted of a 5×5×5 mm³ 200×200×200 voxels. As a result, the generated dose represented the dose distribution within 1×1×1 m³. When the gamma source holder 402 is not being used, it is located inside the source container 412.

Figure 14:
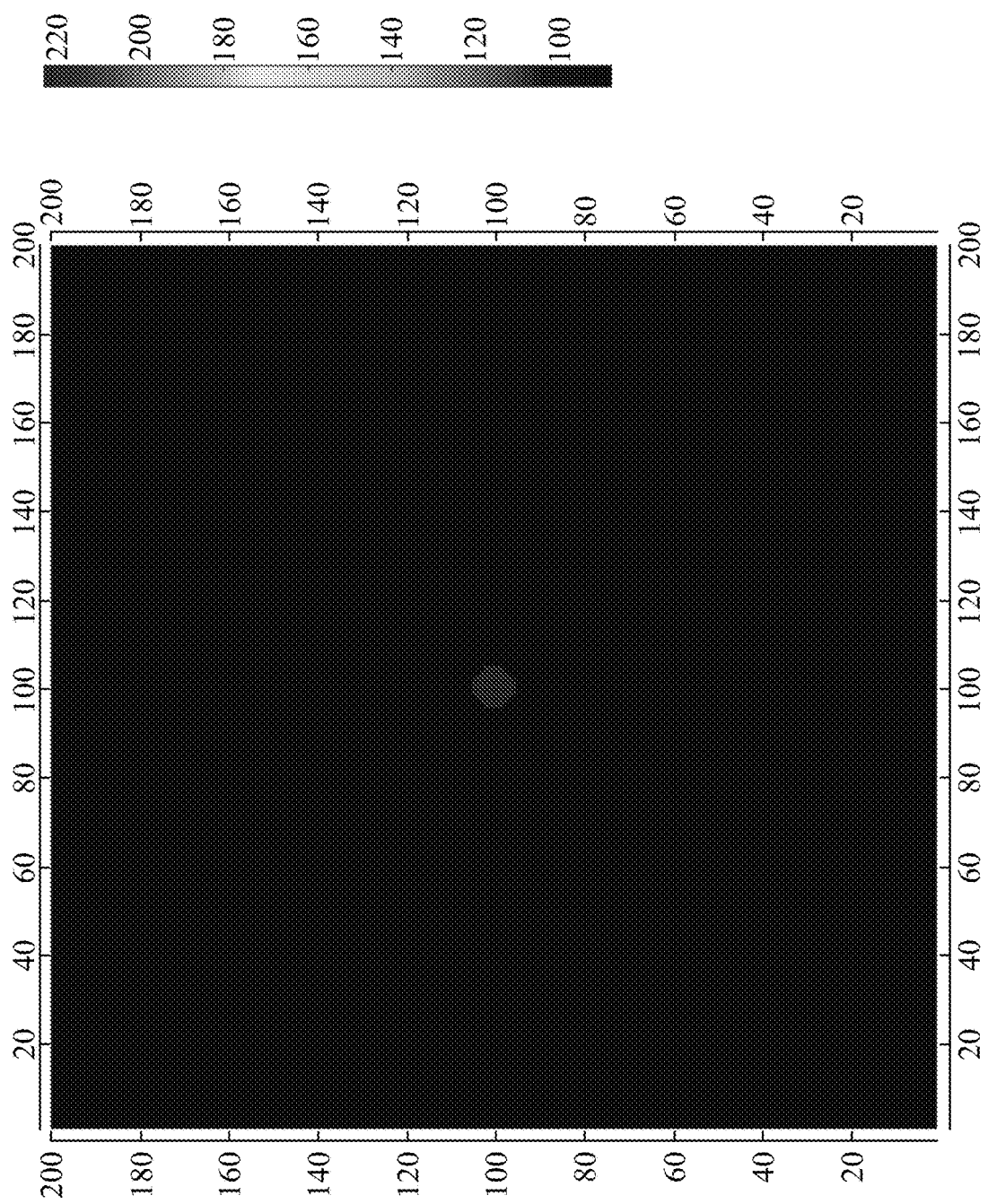
FIG. 14 is an axial dose distribution in mSv/year when the source is in the off position, according to an aspect of the present disclosure.
Figure 15:
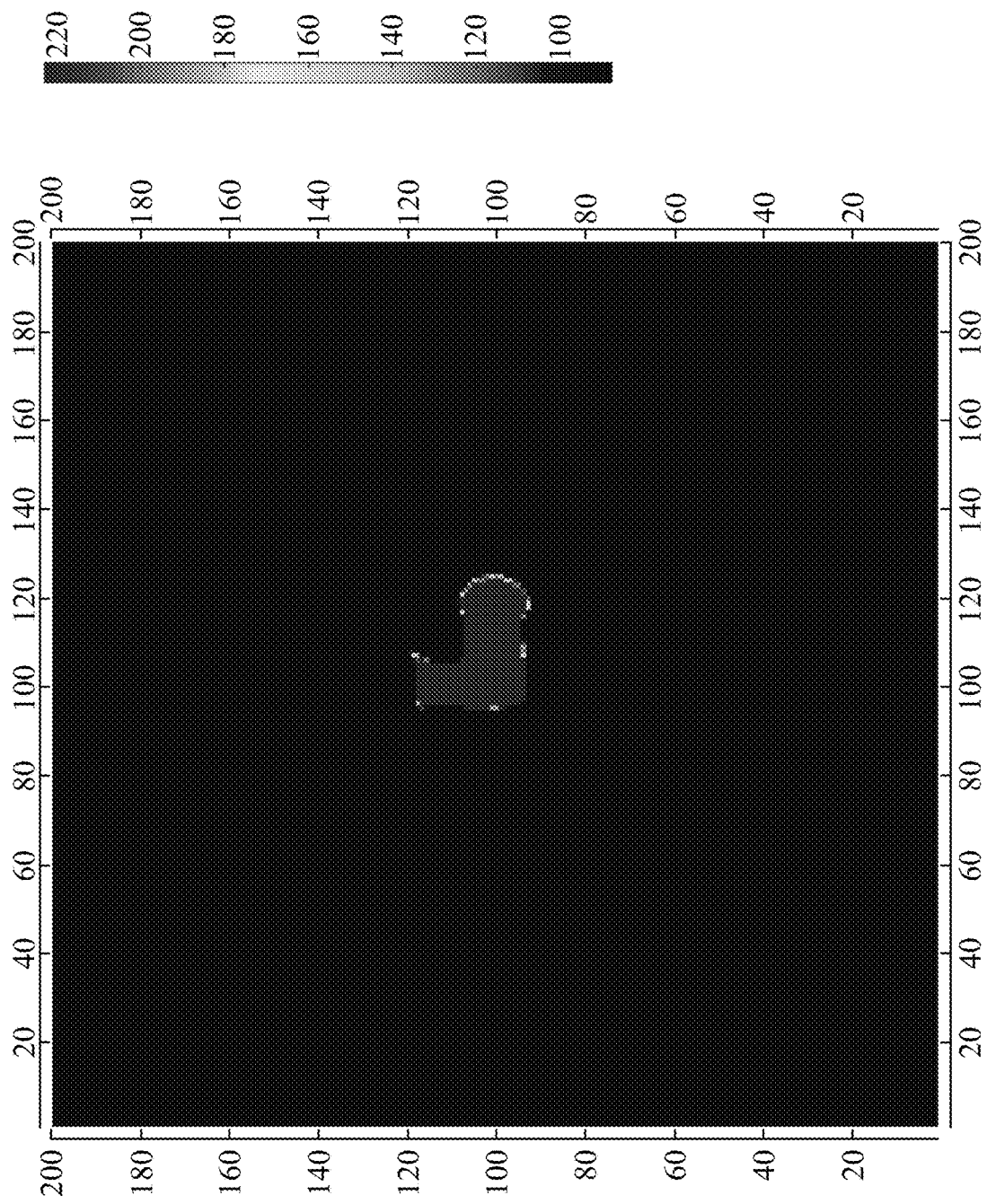
FIG. 15 is a sagittal dose distribution in mSv/year when the source is in the off position, according to an aspect of the present disclosure.

FIG. 14 and FIG. 15 illustrate axial and a sagittal dose distributions, respectively, in mSv/year, at the planes in which the source (gamma radiation material 410) is located when it is not in use (inside the source container 412). The X- and Y-axes represent the voxel number, where each voxel represents a 5 mm distance.

The dose within the source container 412 is high but drops significantly outside to source container 412. The gamma source holder 402 covers the source in all directions except one, providing less attenuation in that direction. Therefore, the dose in that direction is higher outside the container and is up to 3 mSv/year. Nevertheless, the dose in the remaining region outside the container is very low except for some few outliers that are associated with high uncertainty. Uncertainty is high outside the container due to the high efficiency of the shield, which reduces the number of photons penetrating the shield.

Figure 16:
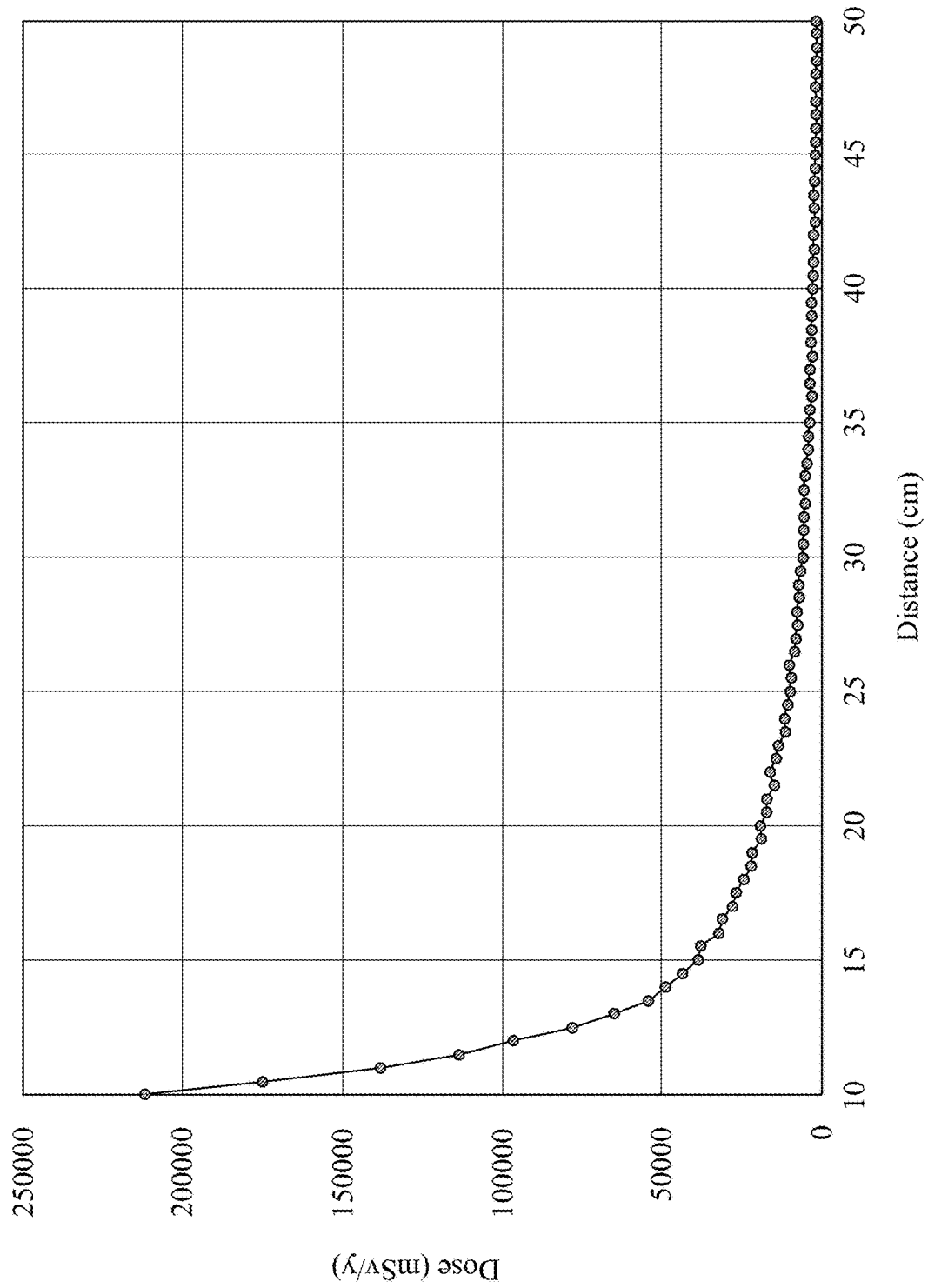
FIG. 16 is a graph illustrating dose profile along a beam central-axis, according to an aspect of the present disclosure.
Figure 17:
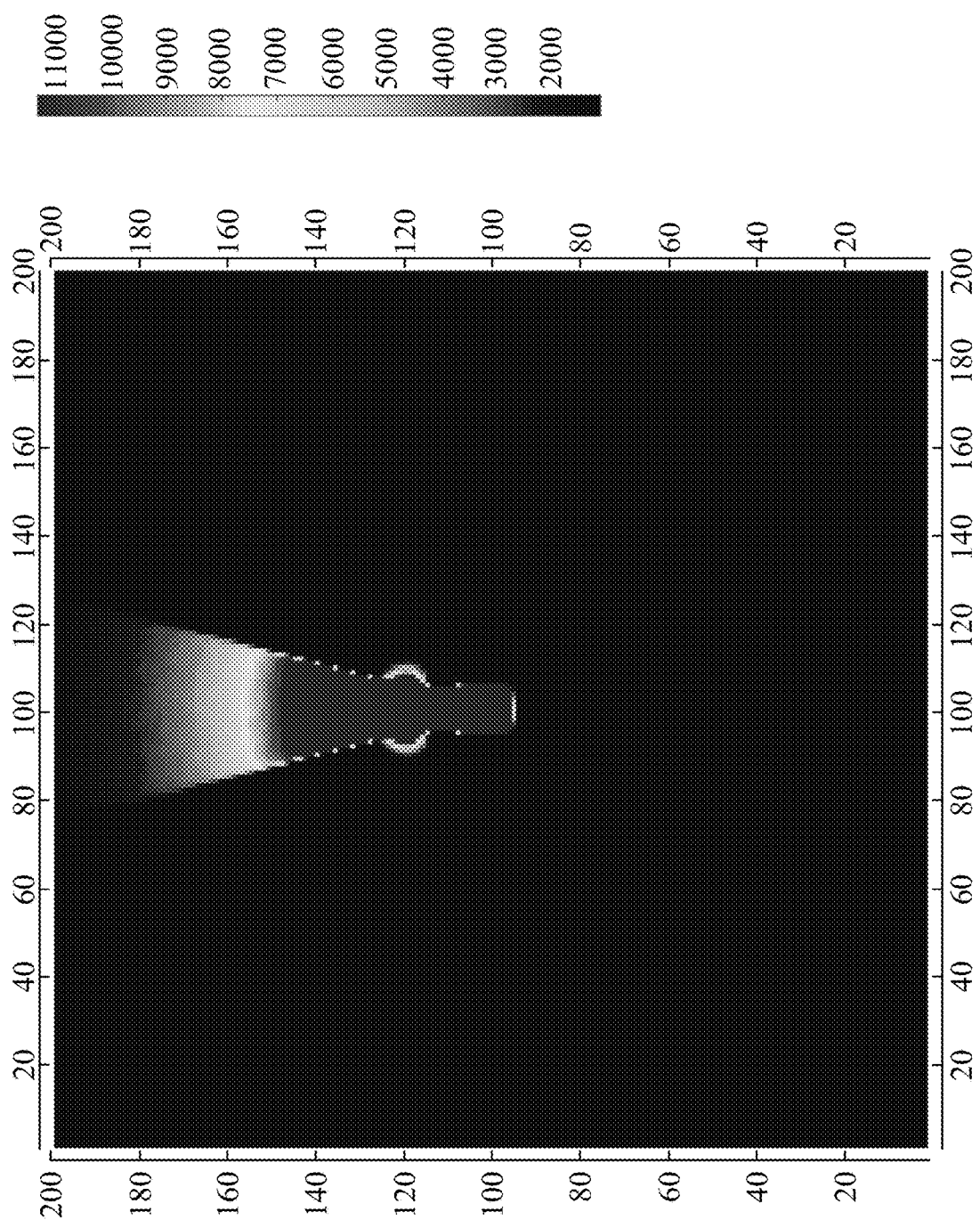
FIG. 17 is an axial dose distribution in mSv/year when the source is in the imaging position, according to an aspect of the present disclosure.
Figure 18:
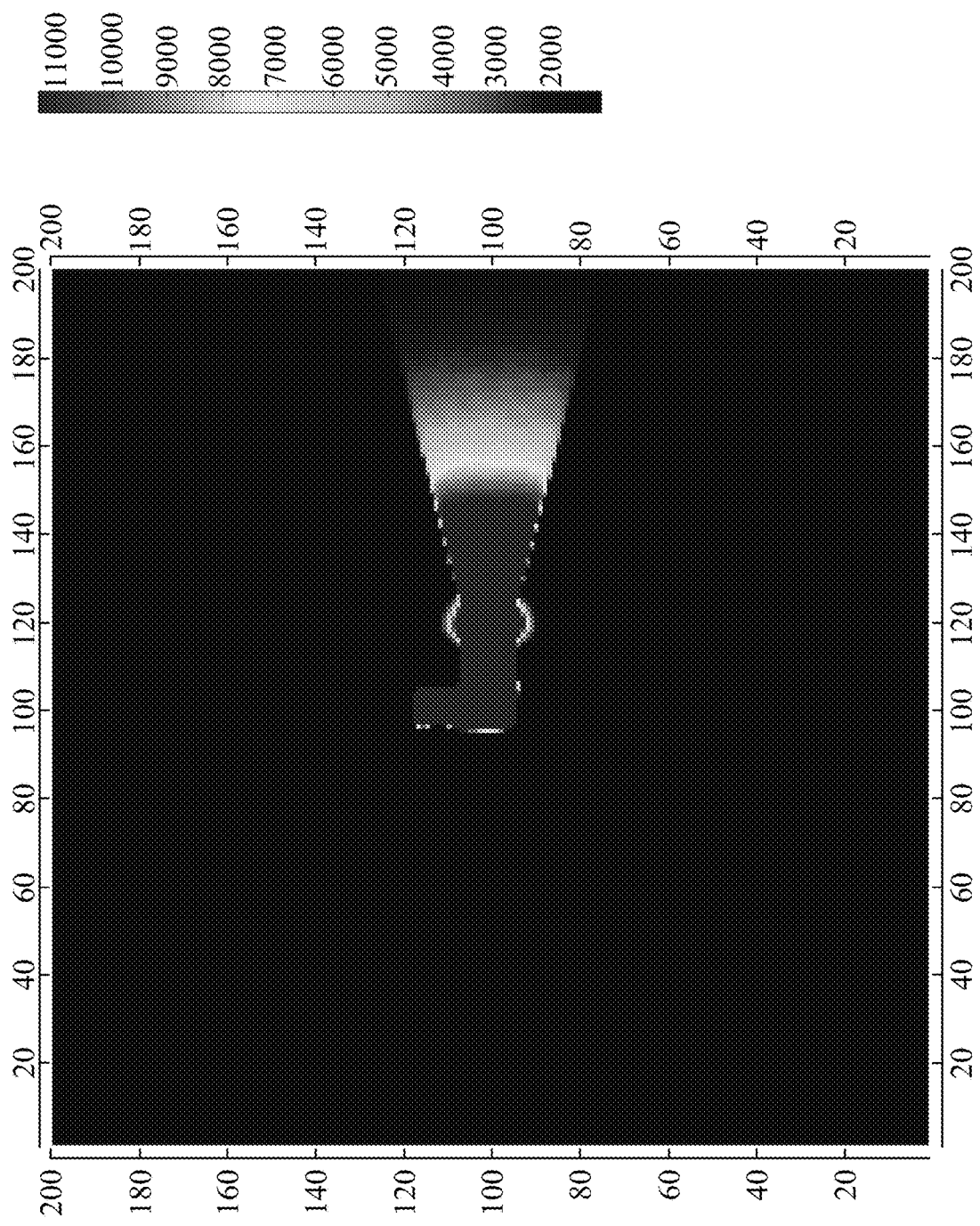
FIG. 18 is a sagittal dose distribution in mSv/year when the source is in the imaging position, according to an aspect of the present disclosure.

Further, the source was moved into the imaging position to determine the dose distribution outside the field of view and around the system. Areas outside the beam of view and in the beam path direction have a maximum dose of 3 mSv/year. Behind and on the sides of the system 100, the dose was mostly negligible and associated with high uncertainty due to effective shielding. In the beam field of view, the dose along the central line is illustrated in FIG. 16, while the axial and sagittal dose distributions are depicted in FIG. 17 and FIG. 18, respectively. While the dose distribution maps show the shielding to be effective for Gd-153, other lower energy sources are expected to be used more frequently with the system 100. This is due to Gd-153 high energy that may limit its applications.

Furthermore, an image quality assessment phantom was created in simulation to provide a relative assessment of the quality of the images produced by the gamma imaging system to those produced by X-ray machines. The phantom was composed of 12 mm polymethyl methacrylate "PMMA" and consisted of four regions. The first region contained lead line-pairs ranged from 0.6 to 5 lp/mm to assess resolution. The second region contained low contrast objects of different thicknesses and diameters, and the third region was a copper step-wedge, consisted from 7 steps with thicknesses ranging from 0.3 to 2.8 mm, while the fourth region consisted of 5 steps of equal thickness but different composition (lung, adipose, muscle, PMMA, bone).

Figure 19A:
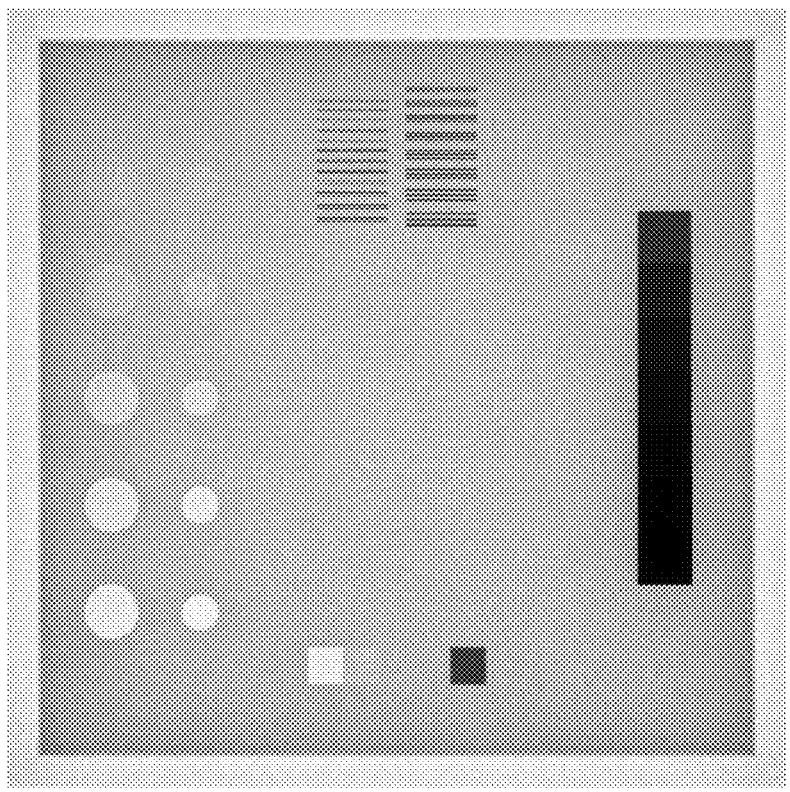
FIG. 19A is a radiography image produced with Am-241, according to an aspect of the present disclosure.
Figure 19B:
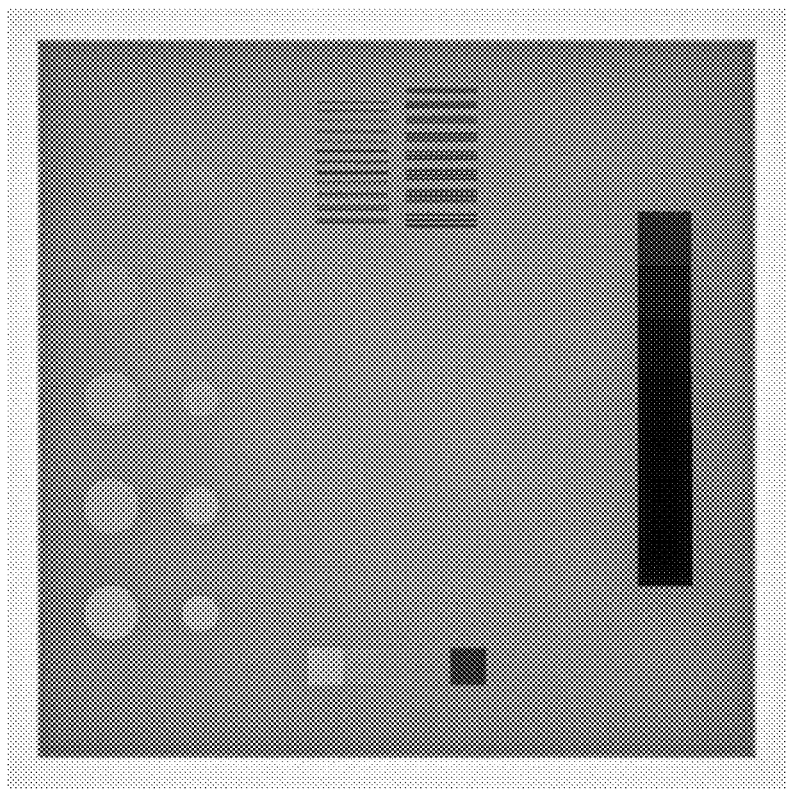
FIG. 19B is a radiography image produced with Gd-153, according to an aspect of the present disclosure.
Figure 20A:
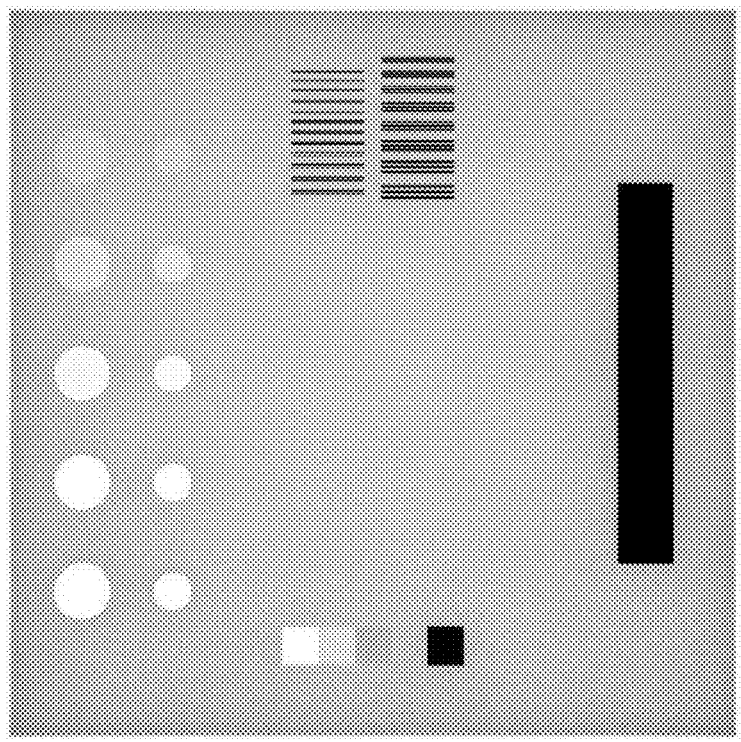
FIG. 20A is a radiography image produced with 60 kVp, according to an aspect of the present disclosure.
Figure 20B:
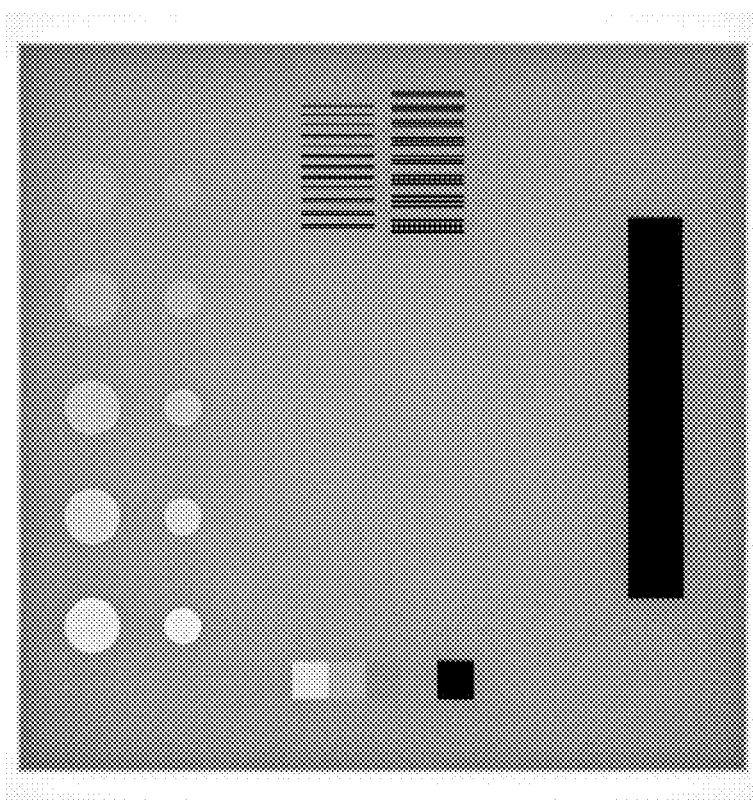
FIG. 20B is a radiography image produced with 80 kVp, according to an aspect of the present disclosure.

Images were produced with a selenium flat panel detector with a 0.1 mm pixel size and with 4 different sources: 60 kVp, 80 kVp, Gd-153 and Am-241. All images were acquired at 80 cm distance. Gamma-ray images were acquired with a cylindrical source of 2 mm height and 3 mm diameter. An image quality comparison is presented in Table 5. Gamma-ray sources penumbra was reduced by using an 80 cm source to image distance. However, X-ray resolution remained higher due to the smaller source size. FIG. 19A shows images produced with AM-241 and FIG. 19B shows images produced with Gd-153. FIG. 20A shows images produces at an intensity of 60 kVp and FIG. 20B shows images produced at an intensity of 80 kVp. The images presented in FIG. 19A, FIG. 19B, and FIG. 20A and FIG. 20B show X-ray and gamma-ray images of the gamma radiography system of the present disclosure to be of comparable quality for different sources and intensities. While Am-241 showed a higher dynamic range than the other sources, X-rays produced smoother images than gamma-ray.

TABLE 1

Image quality comparison between images acquired with different sources

| Source | Limiting resolution (lp/mm) | No of distinguishable copper steps | Number of visible low contrast objects | No of distinguishable tissue |
|---|---|---|---|---|
| 60 kVp | 2.8 | 4 | 10 | 4 |
| 80 kVp | 2.8 | 5 | 10 | 4 |
| Am-241 | 2.5 | 7 | 10 | 4 |
| Gd-153 | 2.5 | 5 | 10 | 3 |

To this end, the present disclosure provides a gamma radiography system 100 that is lightweight and portable; simple in construction and flexible; can encapsulate sources of different sizes; provide sufficient shielding to protect the patient, worker, and public; and provides ease of handling, movement, and replacement of source material. The system 100 overcomes the requirement of complicated electronic setup or high voltage generator.

Obviously, numerous modifications and variations of the present disclosure are possible in light of the above teachings. It is therefore to be understood that within the scope of the appended claims, the invention may be practiced otherwise than as specifically described herein.

The invention claimed is:

1. A gamma radiography system, comprising:
   a gamma source holder;
   a shaft handle attached at a first end to the gamma source holder;
   a source container configured to surround the gamma source holder, wherein the source container is cylindrical;
   a source container cover attached to a first opening of the source container, wherein the source container cover is configured to receive and slidingly support the shaft handle;
   a second opening of the source container, wherein the second opening is configured with threads;
   a shielded housing having four walls, a floor and a roof, wherein the roof includes a threaded opening configured to attach to the threads of the source container;
   a first wall of the shielded housing including a beam aperture;
   an extension connected to the first wall of the shielded housing, such that an opening of the extension covers the beam aperture, wherein the extension includes a plurality of slots each configured to hold a beam modifying device; and
   the shaft handle is further configured to move the gamma source holder between a non-deployed position, in which the gamma source holder is surrounded by the source container, to a deployed position, in which the gamma source holder extends from the source container into the shielded housing.

2. The gamma radiography system of claim 1, wherein the opening of the extension is welded to a shielded housing surface which surrounds the beam aperture in the first wall.

3. The gamma radiography system of claim 1, wherein an inner surface of the source container, an inner surface of the source container cover and the walls of the shielded housing are lined with a first layer of lead and a second layer of stainless steel, wherein the second layer of stainless steel covers the first layer of lead.

4. The gamma radiography system of claim 1, wherein the beam modifying devices are selected from a group comprising collimators and filters.

5. The gamma radiography system of claim 1, wherein the beam modifying devices include at least one light filter.

6. The gamma radiography system of claim 1, wherein the beam modifying devices include at least one grating filter.

7. The gamma radiography system of claim 1, wherein the beam modifying devices include at least one collimator.

8. The gamma radiography system of claim 1, further comprising:
   a handle grip attached to a second end of the shaft handle, wherein the handle grip is configured with a smooth upper surface and indentations within a lower surface.

9. The gamma radiography system of claim 1, further comprising:
   a gamma radiation material located within the gamma source holder, wherein the gamma radiation material is selected from a group comprising americium 241, gold 195, cadmium 109, cesium 144, cobalt 57, europium 155 and gadolinium 153.

10. The gamma radiography system of claim 1, wherein the source container cover includes a central aperture configured to receive the shaft handle, wherein a diameter of the central aperture is equal to a diameter of the shaft handle plus one millimeter, and wherein a thickness of the source container cover is selected to be in the range of 1 centimeter to 2 centimeters.

11. The gamma radiography system of claim 1, further comprising:
a first plurality of legs connected to an underside of the floor of the shielded housing;
a second plurality of legs connected to an of the extension; and
a plurality of caster wheels connected to the first plurality of legs and the second plurality of legs.

12. The gamma radiography system of claim 11, further comprising:
a shielded housing handle connected to the shielded housing, wherein the shielded housing handle is configured to lift and/or pull the shielded housing to and/or from a radiation station.

13. The gamma radiography system of claim 11, further comprising:
a controller connected to the shielded housing;
an antenna connected to the controller;
a plurality of wheel motors attached to the plurality of caster wheels, wherein the plurality of wheel motors are electrically connected to the controller; and
a remote control device communicatively coupled to the antenna, wherein the remote control device is configured to transmit signals to the antenna for actuating the plurality of wheel motors, wherein the signals are configured to rotate the plurality of wheels of the gamma radiography system.

14. The gamma radiography system of claim 13, further comprising:
a linear motor operatively connected to the shielded housing and the shaft handle, wherein the linear motor is configured to raise or lower the shaft handle to move the gamma source holder from the non-deployed position to the deployed position respectively.

15. The gamma radiography system of claim 14, wherein the remote control device is further configured to transmit commands for actuating the linear motor to the antenna, wherein the controller is configured to actuate the linear motor to raise or lower the shaft handle.

16. A method for using a gamma radiography device, comprising:
placing a gamma source material in a gamma source holder, wherein the gamma source holder is attached to a first end of a shaft handle;
placing the gamma source holder in a source container;
inserting a second end of the shaft handle through a central aperture of a source container cover;
screwing threads on the source container to threads of a roof of a shielded housing;
installing a handle grip on the second end of the shaft handle;
transporting the gamma radiography device to a radiation station;
inserting at least one beam modifying device into an extension of the shielded housing;
placing the gamma source holder into a deployed position by lowering the shaft handle towards the shielded housing until the source holder contacts a floor of the shielded housing;
keeping the gamma source holder in the deployed position for a desired imaging interval; and
placing the gamma source holder into a non-deployed position by raising the shaft handle away from the shielded housing until the gamma source holder contacts the source container cover.

17. The method for using a gamma radiography device of claim 16, wherein transporting the gamma radiography device to the radiation station comprises:
transmitting, with a remote control device, direction commands;
receiving, by an antenna coupled to a controller, the direction commands;
actuating, by the controller, a plurality of wheel motors connected to a plurality of caster wheels located on legs of the shielded housing and extension until the gamma radiography device docks into the radiation station.

18. The method for using a gamma radiography device of claim 16, wherein transporting the gamma radiography device to the radiation station comprises:
performing one or more of lifting and pulling, by a shielded housing handle, the gamma radiography device to the radiation station.

19. The method for using a gamma radiography device of claim 16, wherein placing the gamma source holder into one of the deployed position and the non-deployed position comprises:
transmitting, with a remote control device, shaft handle direction commands;
receiving, by an antenna coupled to a controller, the shaft handle direction commands;
actuating, by the controller, a linear motor connected to the source container and the shaft handle to one of lower and raise the shaft handle.

20. A method for assembling a gamma radiation device, comprising:
welding an extension to a first wall of a shielded housing, wherein the first wall has a beam aperture configured to pass a gamma radiation beam through the extension;
attaching a first leg to a first corner of an underside of the shielded housing;
attaching a second leg to a second corner of the underside of the shielded housing, wherein the first corner and the second corner are opposite the extension;
attaching a third leg to a center of an underside of the extension;
installing a caster wheel on an end of each leg;
connecting a wheel motor to the caster wheel directly beneath the extension;
placing a gamma source holder attached to a shaft handle in a source container such that a grip end of the shaft handle extends through a central aperture of a source container cover;
screwing threads on the source container to threads of a roof of the shielded housing;
installing a handle grip on the grip end of the shaft handle;
installing a linear motor to the source container and the shaft handle;
installing an antenna on an exterior of the shielded housing;
installing a controller on the exterior of the shielded housing; and
connecting the controller to the antenna, the wheel motor, and the linear motor, wherein the controller is configured to receive, from a remote control device, direction commands and actuate the wheel motor to transport the gamma radiation device to a radiation station based on the direction commands, wherein the controller is further configured to receive, from the remote control device, shaft handle direction commands and actuate the linear motor to one of lower and raise the shaft handle based on the shaft handle direction commands.

* * * * *